United States Patent [19]
Shinnick et al.

[11] Patent Number: 5,478,726
[45] Date of Patent: Dec. 26, 1995

[54] MYCOBACTERIAL RECOMBINANTS AND PEPTIDES

[75] Inventors: Thomas Shinnick, Atlanta, Ga.; Richard Houghten, Solana Beach, Calif.

[73] Assignee: The Scripps Research Institute, La Jolla, Calif.

[21] Appl. No.: 993,815

[22] Filed: Dec. 18, 1992

Related U.S. Application Data

[60] Continuation of Ser. No. 574,439, Aug. 28, 1990, which is a division of Ser. No. 159,667, Feb. 24, 1988, Pat. No. 4,976,958, which is a continuation-in-part of Ser. No. 19,529, Feb. 26, 1987, Pat. No. 4,952,395.

[51] Int. Cl.⁶ .................. G01N 33/50; G01N 33/569; A61K 38/04; A61K 39/04
[52] U.S. Cl. .................. 435/724; 436/503; 424/190.1; 424/248.1; 530/326; 530/327
[58] Field of Search .................. 435/7.24; 436/503; 530/326, 327; 424/190.1, 248.1

[56] References Cited

U.S. PATENT DOCUMENTS

| | | | |
|---|---|---|---|
| 4,769,237 | 9/1988 | Bittle et al. ............... | 424/88 |
| 4,906,742 | 3/1990 | Young et al. ............... | 536/27 |

OTHER PUBLICATIONS

Atassi et al., "Chap 1: A Comparison of T Cell and B Cell Recognition of Defined Protein Antigens", in *Antigen–Specific T Cell Receptors and Factors*, ed. J. J. Marchalonis, pp. 37–51+55–63 (1987).
Sela, *Adv. Immunol.*, vol. 5, pp. 115–117 (1966).
*Current Communications in Molecular Biology, Immune Recognition of Protein Antigens*, Laver et al., eds., Cold Spring Harbor Lab., N.Y. pp. 71–76; 156–160.
Francis et al., *Vaccines* 88, Ginsberg et al., eds., Cold Spring Harbor Lab., N.Y. (1988) pp. 1–7.
Francis et al., *Vaccines* 87, Chanock et al., Eds., Cold Spring Harbor Lab., N.Y. (1987) pp. 60–67.
Germain, R. N., "The Ins and Outs of Antigen Processing and Presentation," Nature 322:687–689 (1986).
Schwartz, R. H., "Fugue in T–Lymphocyte Recognition", Nature 326:738–739 (1987).
Young et al., "Dissection of *Mycobacterium tuberculosis* antigens using recombinant DNA", Proc. Natl. Acad. Sci. 82:2583–2587 (1985).
Spouge et al., "Strong conformational propensities enhance T cell antigenicity," J. Immunol 138:204–212 (1987).
Berzofsky, J. A., "Intrinsic and extrinsic factors in protein antigenic structure," Science 229:932–940 (1985).
DeLisi et al., "T–cell antigenic sites tend to be amphipathic structures," Proc. Natl. Acad. Sci. 82:7048–7052 (1985).
Fatham et al., *Ann. Rev. Immunol.*, 1:633–655 (1985).
Portions of computer–assisted search, File 154:Medline.
General Index p. 392, title and copyright pages of the ATCC catalogue of Cell Lines and Hybridomes for 1988.
Bittle et al., *Nature*, 298:30–33 (Jul., 1982).
Finnegan et al., "The T cell repertoire for recognition of a phylogenetically distant . . . ," J. Exp. Med. 164:897–910 (1986).
Shinnick et al., *Infect. Immun.*, 55:1932–1935 (Aug., 1987).
Gillis et al., *Infect. Immun.*, 37:172–178 (1982).
Gillis et al., *Infect. Immun.*, 49:371–377 (1985).
Mustafa et al., *Lepr. Rev.*, 57, Suppl. 2:123–130 (1986).
Thole et al., *Infect. Immun.*, 50:800–806 (1985).
Emmerich et al., *J. Exp. Med.*, 163:1024–1029 (1986).
Mehra et al., *Proc. Natl. Acad. Sci. USA*, 83:7013–7017 (1986).
Engers (Rapporteur), *Infect. Immun.*, 51:718–720 (1986).
Young et al., *Nature*, 316:450–452 (1985).
Mustafa et al., *Nature*, 319:63–66 (1986).
Boom et al., *Infect. Immun.*, 55:2223–2229 (Sep. 1987).
Kaufmann et al., *Eur. J. Immunol.*, 17:351–357 (1987).
Melancon–Kaplan et al., *Proc. Natl. Acad. Sci., USA*, 85:1917–1921 (Mar. 1988).
Lu et al., *Infect. Immun.*, 55:2378–2382 (Oct. 1987).
Kingston et al., *Infect. Immun.*, 55:3149–3154 (Dec. 1987).
Oftung et al., *J. Immunol.*, 141:2749–2754 (1988).

*Primary Examiner*—Michael P. Woodward
*Attorney, Agent, or Firm*—Welsh & Katz, Ltd.

[57] ABSTRACT

Recombinant 540 amino acid residue and 517 amino acid residue proteins encoded by the genome of *Mycobacterium tuberculosis* are disclosed as are vectors for propagating their DNA sequences and expressing the proteins. Also disclosed are methods for using those proteins. Peptides that correspond substantially to the sequences of those proteins and methods of their use are also disclosed, as are polymers containing peptide repeating units corresponding to the 540 residue protein and also polymers containing 517 protein pentapeptides as repeating units.

5 Claims, 7 Drawing Sheets

FIG.2a

```
I   I   A   E   D   V   E   G   E   A   L   S   T   L   V   N   K   I   R   G   T   F   K   S   V   A   V   K   A   P   G   F   G   D   R   R
TCATCGCCGAGGACGTCGAGGGCGAGGGCCTCGTCCACCCTGGTCGTCAACAAGATCCGCGGCACCTTCAAGTCGGTGGCGGTCAAGGCTCCCGGCTTCGGCGACCGCCGC  1100
AGTAGCGGCTCCTGCAGCTCCCGCTCCCGCTCCCGCAGTCGGGACCAGCAGTTGTTCTAGGCGCCGTGGAAGTTCAGCAGCCACCGCCAGTTCCGAGGGCCGAAGCCGCTGGCCGCG  1210
      1000                   1010                    1020                1030           1040            1050        1060         1070          1080             1090

K   A   M   L   Q   D   M   A   I   L   T   G   G   Q   V   I   S   E   E   V   G   L   T   L   E   N   A   D   L   S   L   L   G   K   A   R   K
AAGGCGATGCTGCAGGATATGGCCATTCTCACCGGTGGTCAGGTGATCAGCGAAGAGTCGGCCTGACGCTGGAGAACGCCGACCTGTCGCTGCTAGGCAAGGCCCGCAA  1200
TTCCGCTACGACGTCCTATACGGTAAGAGTGGCCACCAGTCCACTAGTCGCTTCTCAGCCGGACTGCGACCTCTTGCGGCAGCGACGATCCGTTCCGGGCGTT  1210
     1110                  1120              1130               1140                1150              1160            1170           1180            1190

V   V   V   T   K   D   E   T   T   I   V   E   G   A   G   D   T   D   A   I   A   G   R   V   A   Q   I   R   Q   E   I   E   N   S   D   S
GGTCGTGGTCACCAAGGACGAGACCACCATCGTCGAGGGCGCCGGTGACACCGACGCCATCGCCGGACGAGTGGCCCAGATCCGCCAGGAGATCGAGAACAGCGACTCCG  1320
CCAGCACCAGTGGTTCCTGCTCTGGTGGTAGCAGCTCCCGCGGCCACTGTGGCTGCGGTAGCGGCCTGCTCACCGGGTCGTCTAGCTCTTGTCGCTGAGCC  1320
      1220                     1230                 1240                1250              1260               1270              1280              1290               1300               1310

D   Y   D   R   E   K   L   Q   E   R   L   A   K   L   A   G   G   V   A   V   I   K   A   G   A   A   T   E   V   E   L   K   E   R   K   H   R
ACTACGACCGTGAGAAGCTGCAGGAGCGCCTGGCCAAGCTGGCCGGTGGTGTCGCGGTGATCAAGGCCGGTGCCGCCACCGAGGTCGAACTGAAGGAGCGCAAGCACCGC  1430
TGATGCTGGCACTCTTCGACGTCCTCGCGGACCGGTTCGACCGGCCACCACAGCGCCACTAGTTCCGGCCACGGCGGTGGCTCCAGCTTGACTTCCTCGCGTTCGTGGCG  1430
     1330                 1340              1350               1360           1370             1380                1390             1400             1410              1420

I   E   D   A   V   R   N   A   K   A   A   V   E   E   G   I   V   A   G   G   V   T   L   L   Q   A   A   P   T   L   D   E   L   K   L   E
ATCGAGGATGCGGTTCGCAATGCCAAGGCCGCCGTTGAAGGTGGCATCGTCGCCGGAGGCGTGACGCTGCTGCAAGCGGCCCCGACCCTCGACGAGCTGAAGCTCGA  1540
TAGCTCCTACGCCAAGCGTTACGGTTCCGGCGGCAACTTCCACCGTAGCAGCGGCCTCCGCACTGCGACGACGTTCGCCGGGGCTGGGAGCTGCTCGACTTCGAGCT  1540
     1440             1450               1460             1470            1480          1490             1500               1510           1520               1530

G   D   E   A   T   G   A   N   I   V   K   V   A   L   E   A   P   L   K   Q   I   A   F   N   S   G   L   E   P   G   V   A   E   K   V
AGGGCGACGAGGCGACCGGCGCCAACATCGTGAAGGTGGCGCTGGAGGCCCCGCTGAAGCAGATCGCCTTCAACTCCGGGCTGGAGCCGGGTGTGGCCGAGAAGGTGC  1650
TCCGCTGCTCCGCTGGCCGCGGTTGTAGCACTTGTAGCACTTCCAGCGCGACCTCCGGGGCGACTTCGTCTAGCTAGCGGAAGTTGAGGCCCGACCTCGGCCCACCGGCTCTTCCACG  1650
     1550              1560               1570           1580             1590           1600             1610             1620               1630              1640

R   N   L   P   A   G   H   G   L   N   A   Q   T   G   V   Y   E   D   L   L   A   A   G   V   A   D   P   V   K   V   T   R   S   A   L   Q   N
GCAACCTGCCGGCTGGCCACGGACTGAACGCTCAGACTGGAGTGTCTACGAGGATCTGCTCGCTGCGGGCGTTGCTGACCCGGTCAAGGTGACCCGTTCGGCGCTGCAGAAT  1760
CGTTGGACGGCCGACCGGTGCCTGACTTGCGAGTCTGACCTCACAGATGCTCCTAGACGAGCGACGCCCGCAACGACTGGGCCAGTTCCACTGGGCCAGTTCCAGCAAGCCCGACGTCTTA  1760
     1660            1670               1680             1690            1700             1710              1720              1730             1740             1750

A   A   S   I   A   G   L   F   F   L   T   T   E   A   V   V   A   D   K   P   L   E   K   E   A   S   V   P   G   G   G   D   M   G   G   M   D   F
GCGGCTTCCATCGCGGGTCTGTTCTTCCTGACCACCGAGGCCGTCGTTGCCGACAAGCCGCTCGAGAAAGAGGCTTCCGTTCCCGGTGGCGGCGACATGGGTGGCATGGATTT  1870
CGCCGAAGGTAGCGCCCAGACAAGAAGGACTGGTGGCTCCGGCAGCAACGGCTGTTCGGCCTTTCGGCAGCTCTTTCTCCGAAGGCAAGGGCCACCGCCGCTGTACCCACCGTACCTAAA  1870
     1770              1780            1790           1800            1810            1820             1830             1840              1850             1860

*
CTGACCCCGGGCGAGAAGTCGCAGCCGAGGAGCCCGGTCCCTCTGTTGGGAGCTACGGTACCGAGAACACCGCCAGTCGTTGTAGGCAACCTT
GACTGGGGCCGCTCTTCAGCGTCGGCTCCTCGGGCCAGGGAGGGAAACACCCCCGGGGCCCATGGCTCATGTGCTGTCAGCACATCCGTTGGAA  1980
     1880             1890           1900              1910           1920            1930              1940             1950             1960           1970
```

MYCOBACTERIAL RECOMBINANTS AND PEPTIDES

This invention was made with the support of the United States Government, and the United States Government has certain rights in the invention.

CROSS REFERENCE TO A RELATED APPLICATIONS

This application is a continuation of application Ser. No. 07.574,4389, filed Aug. 28, 1990, which is a division of co-pending application Ser. No. 07,159,667, filed Feb. 24, 1988, now U.S. Pat. No. 4,976,958, which was a continuation-in-part of application Ser. No. 07/019,529, filed Feb. 26, 1987, to issue as U.S. Pat. No. 4,952,395 on Aug. 28, 1990.

TECHNICAL FIELD

The present invention relates to recombinant proteins and peptides related to mycobacteria, and particularly to proteins of *Mycobacterium tuberculosis* that are coded for by adjacent open reading frames on complementary DNA strands of the genome and vectors for propagating and expressing those recombinants, as well as to peptides that correspond substantially in sequence to portions of those proteins.

BACKGROUND ART

The mycobacteria are a diverse collection of acid-fast, gram-positive bacteria some of which cause important human and animal diseases [reviewed in Bloom et al., (1983), *Rev. Infect. Dis.*, 5:765–780; and Chaparas, (1982), *CRC Reviews in Microbiology*, 9:139–197]. In man, the two most common mycobacteria-caused diseases are tuberculosis and leprosy, which result from infections with *Mycobacterium tuberculosis* and *Mycobacterium leprae*, respectively. These two diseases afflict more than 65 million individuals world-wide and result in over 4 million deaths annually, Bloom et al., (1983), *Rev. Infect. Dis.*, 5:765–780.

The pathogenicity of these mycobacterial infections is closely tied to the host's immune response to the invading mycobacterium [Chaparas, (1982,), *CRC Reviews in Microbiology*, 9:139–197; Collins, (1982), *Am. Rev. Respir, Dis.*, 125:42–49; Dannenberg, (1982), *Am. Rev. Respit. Dis.*, 125:25–29; and Grange, (1984), *Adv. Tuberc. Res.*, 21:1–78]. Not only does *M. tuberculosis* infect and grow within cells of the host's immune system, primarily the aveolar macrophage, but also it is the host's cellular immune response that plays the key roles in immunity from infection, containment of the infection at the initial focus of infection, progression or regression of the infection, and tissue damage or destruction at the foci of infection [Chaparas, (1982), *CRC Reviews In Microbiology*, 9:139–197; Collins, (1989,), *Am. Rev. Respir. Dis.*, 125:42–49; Dannenberg, (1987), *Am. Rev. Respit. Dis.*, 125:25–29; and Grange, (1984), *Adv. Tuberc. Res.*, 21:1–78]. In addition, the standard method of detecting an *M. tuberculosis* infection, the tuberculin skin test, actually measures the host's cellular immune response to the mycobacterium [Snider, (1982), *Am. Rev. Respir. Dis.*, 125:108–118]. The mycobacterial components that are important in eliciting the cellular immune response are not yet well defined.

A number of studies have attempted to define the mycobacterial antigens by standard biochemical and immunological techniques including the analysis of the target antigens of monoclonal hybridoma antibodies directed against mycobacteria [Daniel et al., (1978), *Microbiol. Rev.*, 42:84–113; Engers et al., (1985), *Infect. Immun.*, 48:603–605; Engers et al., (1986), *Infect. Immun.*, 51:718–720; Grange, (1984), *Adv. Tuberc. Res.*, 21:1–78; Ivanyi et al., (1985), *Monoclonal Antibodies Against Bacteria* (A. J. L. and E. C. Macario, eds.) Academic Press, Inc. New York. pp. 59–90; and Stanford, (1983), *The Biology of the Mycobacteria* (Ratledge and Stanford, eds.), Academic Press, London, vol. 9., pp. 85–127].

One particular antigen, a 65 kilodalton (KD) protein, is present in a wide range of mycobacterial species and has been most intensively studied as an antigen of *M. leprae* [Emmrich et al., (1986), *J. Exp. Med.*, 163:1024–1029; Gillis et al., (1985), *Infect. Immun.*, 49:371–377; Young et al., (1985), *Nature*, 316:450–459; and Mehra et al., (1986) *Proc. Natl. Acad. Sci. USA*, 83: 7013–7017]. This antigen has been designated the 65KD antigen or the cell wall protein-a (CWP-a) antigen since it appears to a co-purify with cell walls in some isolation procedures [Gillis et al., (1985), *Infect. Immun.*, 49:371–377].

In Western blot assays, monoclonal antibodies directed against this antigen react with two major components in an *M. leprae* extract that migrate with apparent sizes of 55,000 and 65,000 daltons, and react occasionally with smaller components as well [Engers et al., (1985), *Infect. Immun.*, 48:603–605 and Gillis et al., (1985), *Infect. Immun.*, 37:172–178]. It is not known if these species represent discrete proteins or precursors and products, or result from chemical or enzymatic cleavage during isolation. In other species, such as *M. gordonae*, only a single species of about 65,000 daltons is detected with the monoclonal antibodies [Gillis et al., (1985), *Infect. Immun.*, 49:371–377].

The 65KD antigen is one of the major immunoreactive proteins of the mycobacteria. This antigen contains epitopes that are unique to a given mycobacterial species as well as epitopes that are shared amongst various species of mycobacteria [Engers et al., (1985), *Infect. Immun.*, 48:603–605 and Gillis et al., (1985), *Infect. Immun.*, 49:371–377]. In addition, some other antigens that appear to be expressed by only one mycobacterial species are also found to contain epitopes expressed in other mycobacterial species. [Kingston et al., (1987) *Infect. Immun.*, 55:3149.]

As discussed hereinafter, it is now found that purified 65KD antigen can elicit a strong delayed-type hypersensitivity reaction in experimental mammals infected with *M. tuberculosis*. Antibodies directed against this protein can also be detected in the sera of patients with tuberculosis or leprosy, and T-cells reactive with this antigen can be isolated from patients with leprosy or tuberculosis as well as from BCG-vaccinated persons [Emmrich et al., (1986), *J. Exp. Med.*, 163:1024–1029; Engers et al., (1986), *Infect. Immun.*, 51:718–720; Mustafa et al., (1986), *Nature*, 319:63–66; and Thole et al., (1985), *Infect. Immun.*, 50:800–806]. Overall, the 65KD antigen appears to be a major, medically important B- and T-cell immunogen and antigen in humans.

BRIEF SUMMARY OF THE INVENTION

The present invention relates to DNA sequences, vectors containing the DNA sequences, proteins, recombinant proteins, peptides, their method of manufacture and use that relate to a *Mycobacterium tuberculosis*. More particularly, those DNA sequences, vectors, proteins, recombinants and peptides relate to two proteins denominated the 540 (65KD)

and 517 proteins that are coded for by adjacent open reading frames on complementary DNA strands of the mycobacterial genome. The peptides correspond substantially to portions of those proteins.

One embodiment of the invention contemplates an isolated DNA molecule that consists essentially of a nucleotide sequence, from right to left and in the direction from 5'-end to 3'-end, corresponding to the sequence represented by the formula of FIG. 2 from about position 3950 to about position 2390 and in a consistent reading frame coding for a 517 amino acid residue protein of *Mycobacterium tuberculosis*. More preferably, that sequence extends from position 3948 through position 2398.

A plasmid vector that comprises a replicon operationally linked to a foreign DNA sequence such as that above and that is capable of replicating that foreign DNA sequence in a replication/expression medium is also contemplated herein, particularly where the replication/expression medium is a unicellular organism, such as a bacterium like *E. coli*. The plasmid vector typically includes sequence-encoded signals for initiation and termination of transcription that are operationally linked to the foreign DNA sequence and are compatible with the replication/expression medium for transcribing a product coded for by the foreign DNA sequence. Further, it can include a translation initiation codon and a translation termination codon, each of which is operationally linked to the 5'-end and the 3'-end, respectively, of the DNA sequence, and are compatible with the replication/expression medium for expressing a protein product coded for by the foreign DNA sequence.

Still further, the 5'-end of the foreign DNA sequence can be operationally linked in translational reading frame to the 3'-end of a second DNA sequence that codes for a second protein or protein fragment or portion, such as the beta-galactosidase molecule. The protein product expressed by that vector is thus a fusion protein that contains the second protein or protein fragment or portion at the amino-terminus and the first-named protein at the carboxy-terminus of the fusion protein; i.e., the fragment or portion of the second protein is at the amino-terminus of the first-named protein.

A culture comprising bacteria that contain a previously described plasmid vector in an aqueous medium appropriate for the expression of the 517 amino acid residue protein of *M. tuberculosis* is also contemplated.

The present invention further contemplates a method for producing a 517 amino acid residue protein of *M. tuberculosis*. That method comprises the steps of culturing a replication/expression medium containing a plasmid vector for replicating and expressing foreign DNA sequence contained therein. That vector contains a foreign DNA sequence that corresponds substantially to the previously mentioned DNA molecule that encodes the sequence of the 517 *M. tuberculosis* protein. The vector also contains operatively linked nucleotide sequences regulating replication and expression of the foreign DNA sequence. The culturing is carried out under conditions suitable for expression of the protein that is encoded by the foreign DNA. The expressed protein encoded by that foreign DNA sequence is thereafter harvested. Culture is typically carried out using unicellular organisms as the replication/expression medium. Such unicellular organism are typically bacteria as described previously.

A method for determining previous immunological exposure of a mammalian host to *Mycobacterium tuberculosis* or *Mycobacterium bovis* is also contemplated. This method comprises the following steps. An inoculum that consists essentially of the purified 65KD (540) protein or an immunologically active portion thereof coded for by the DNA sequence of FIG. 2 is administered intradermally to an assayed mammalian host. That protein is dissolved or dispersed in a physiologically tolerable diluent and is present in that diluent in an amount effective to induce erythema and induration in a mammalian host previously immunized with *M. tuberculosis* or *M. bovis*. The mammal is maintained for a time period of about 24 to about 72 hours, and thereafter is assayed for the presence of erythema and induration at the site of the intradermal administration at the end of that time period. In one aspect of this method the purified 65KD protein is obtained from a mycobacterium such as *M. tuberculosis*. In another aspect of this method, the purified protein is a recombinant 65KD protein, or a recombinant fusion protein that contains a portion of a beta-galactosidase molecule peptide-bonded to the amino-terminus of the 65KD protein, or to the amino-terminus of an immunologically active portion thereof. This type of assay is usually referred to as a delayed cutaneous hypersensitivity (DCH) assay.

Still another aspect of the invention contemplates an inoculum that consists essentially of the purified 65KD (540 amino acid residue) protein antigen or a fusion protein that is coded for by the sequence of FIG. 2. That protein antigen is dissolved or dispersed in a physiologically tolerable diluent, and is present in the diluent in an amount that is effective to induce erythema and induration in a mammalian host previously immunized with *M. tuberculosis* or *M. bovis*. The 65KD protein antigen of the inoculum can be one of the proteins useful in the method described immediately above.

Still a further aspect of the invention is a peptide that consists essentially of a 5 to about 40 amino acid residue sequence that corresponds substantially to a sequence of the 540 amino acid residue protein or the 517 amino acid residue protein coded for by the DNA protein sequence of FIG. 2. More preferably, the peptide contains about 10 to about 20 amino acid residues.

Preferred peptides include those having a sequence, written from left to right in the direction from amino-terminus to carboxy-terminus using single letter symbols, that corresponds to a formula selected from the group consisting of

| | | | | | | | | | | | | | | | | | | |
|---|---|---|---|---|---|---|---|---|---|---|---|---|---|---|---|---|---|---|
| A | V | L | E | D | P | Y | I | L | L | V | S | S | K | V | | | | (22; 211–225); |
| L | L | V | S | S | K | V | S | T | V | K | D | L | L | P | | | | (23; 219–233); |
| L | L | P | L | L | E | K | V | I | G | A | G | K | P | L | | | | (24; 231–245); |
| A | I | L | T | G | G | Q | V | I | S | E | E | V | G | L | | | | (30; 291–305); |
| I | A | F | N | S | G | L | E | P | G | V | V | A | E | K | | | | (46; 451–465) |
| A | R | R | G | L | E | R | G | L | N | A | L | A | D | A | V | K | V | (58; 11–28); |
| E | K | I | G | A | E | L | V | K | E | V | A | K | K | | | | | (59; 67–78); |
| G | L | K | R | G | I | E | K | A | V | E | K | V | T | E | T | L | | (60; 114–130); and |
| I | E | D | A | V | R | N | A | K | A | A | V | E | E | G | | | | (62; 394–408); | wherein each first parenthesized number refers to the Peptide number of Tables 2 and 4, hereinafter, and the second hyphenated numbers refer to the position in the sequence of the 540 amino acid residue-containing protein whose complete amino acid residue sequence and genomic sequence are illustrated in FIGS. 2A and 2B.

Further contemplated is a method for ascertaining the presence of mycobacterially-exposed or mycobacterially-immune, i.e., previously immunologically exposed, mononuclear cells such as T cells in a body sample. Here, mononuclear cells from a mammalian host to be assayed are admixed and contacted in an aqueous cell culture medium with a stimulating amount of both antigen presenting cells and a preferred peptide antigen to form a stimulatory cell culture. That stimulatory cell culture is maintained for a time period sufficient for immune mononuclear cells present to be stimulated and to evidence their stimulation. The presence of mononuclear cell stimulation is thereafter determined. This assay can be carried out in vivo as a DCH assay where the antigen presenting cells are endogenous cells such as macrophages and the aqueous medium is supplied by the blood and lymph. The assay can also be carried out in vitro. A polymer having an above peptide as repeating units can also be used as the antigen.

An assay kit containing a preferred peptide in a container in an amount sufficient to carry out at least one assay as described immediately above is also contemplated.

The invention still further contemplates a vaccine against mycobacteria such as *M. tuberculosis*. The vaccine comprises a physiologically tolerable diluent containing as immunogen an immunizing effective amount of (i) a peptide antigen containing 5 to about 40 residues, and more preferably about 10 to about 20 residues, whose amino acid residue sequence corresponds substantially to a sequence of a mycobacterial 65KD protein and that is capable of stimulating mycobacterially-immune T cells having a phenotype selected from the group consisting of T4$^+$ and T8$^+$ or (ii) a polymer having said peptide antigen as repeating units. Preferably, the mycobacteria is *M. tuberculosis*. The mycobacteria to which the T cells are immune is the same mycobacterial species to which the vaccine is directed.

Yet another aspect of the present invention is a polymer that comprises a plurality of pentapeptide repeating units. Each of those pentapeptide repeating units consists essentially of a sequence, written from left to right in the direction of amino-terminus to carboxy-terminus, represented by a formula N N N I G; or

X G N Z G, wherein X is an amino acid residue selected from the group consisting of F, S, T, L, D, and I; and Z is an amino acid residue selected from the group consisting of T, I, L, S and V. In a further aspect of this invention, the pentapeptide repeating units are bonded together by peptide bonds, whereas in yet another aspect, the pentapeptide repeating units are bonded together by oxidized cysteine residues at the terminii of those repeating units.

BRIEF DESCRIPTION OF THE DRAWINGS

In the drawings forming a portion of this disclosure.

Twenty of the recombinants discussed herein are enumerated along the right-hand margin of the Figure opposite the schematic line representations of the respective genomic portion contained by each recombinant. The lengths and positions of those genomic portions relative to the genome of the 65KD protein are shown by the relative lengths and positions of the lines. Dashes at the termini of the first six shorter lines indicate that those recombinants contained additional base pairs, but the source and sequences of those additional base pairs is presently uncertain.

DNA was isolated from phage stocks of the recombinants expressing the 65KD antigen as described by Helms et al. (1985) *DNA* 4:39–49, and a restriction enzyme cleavage site map was constructed.

Figure 2A:
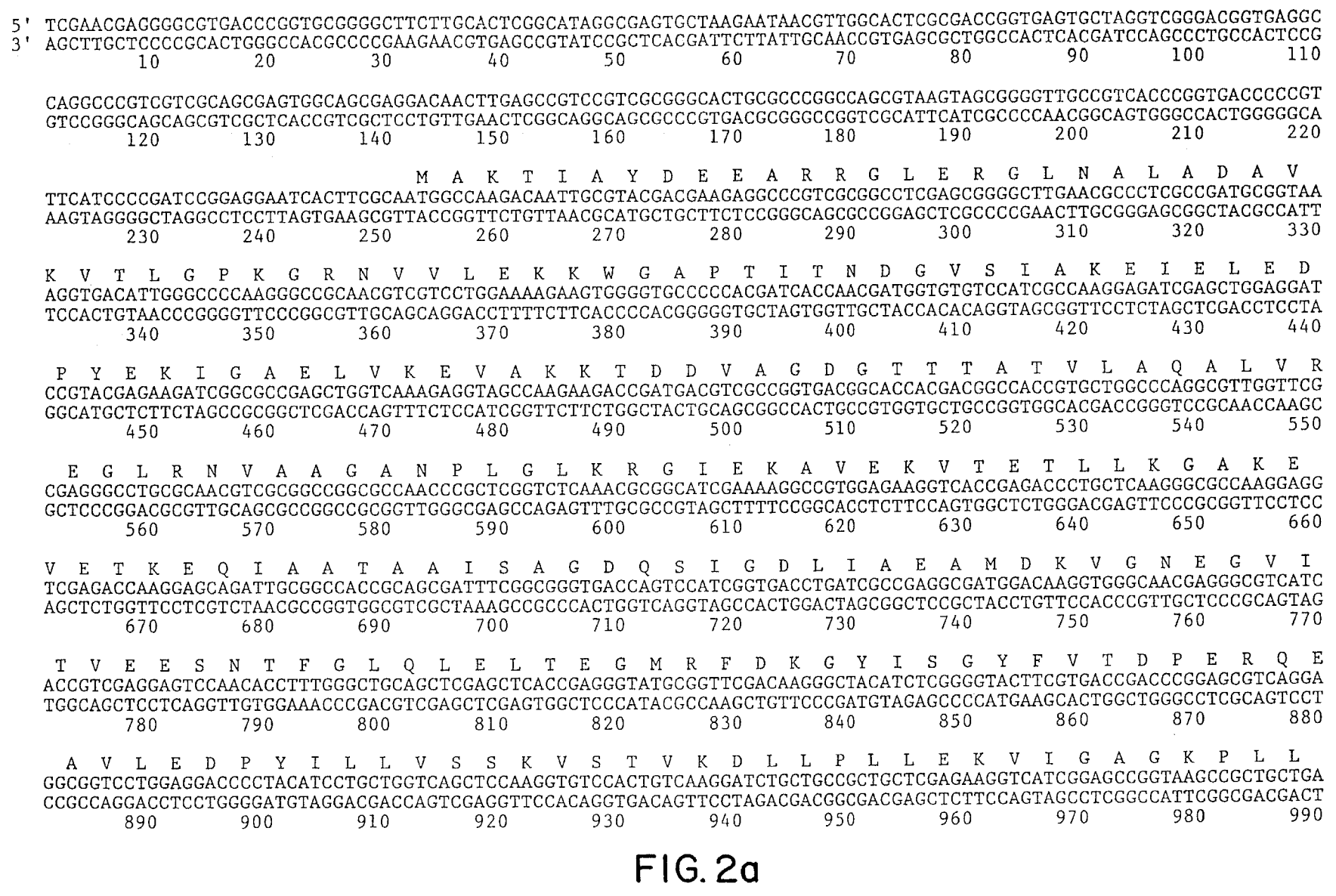
Figure 2C:
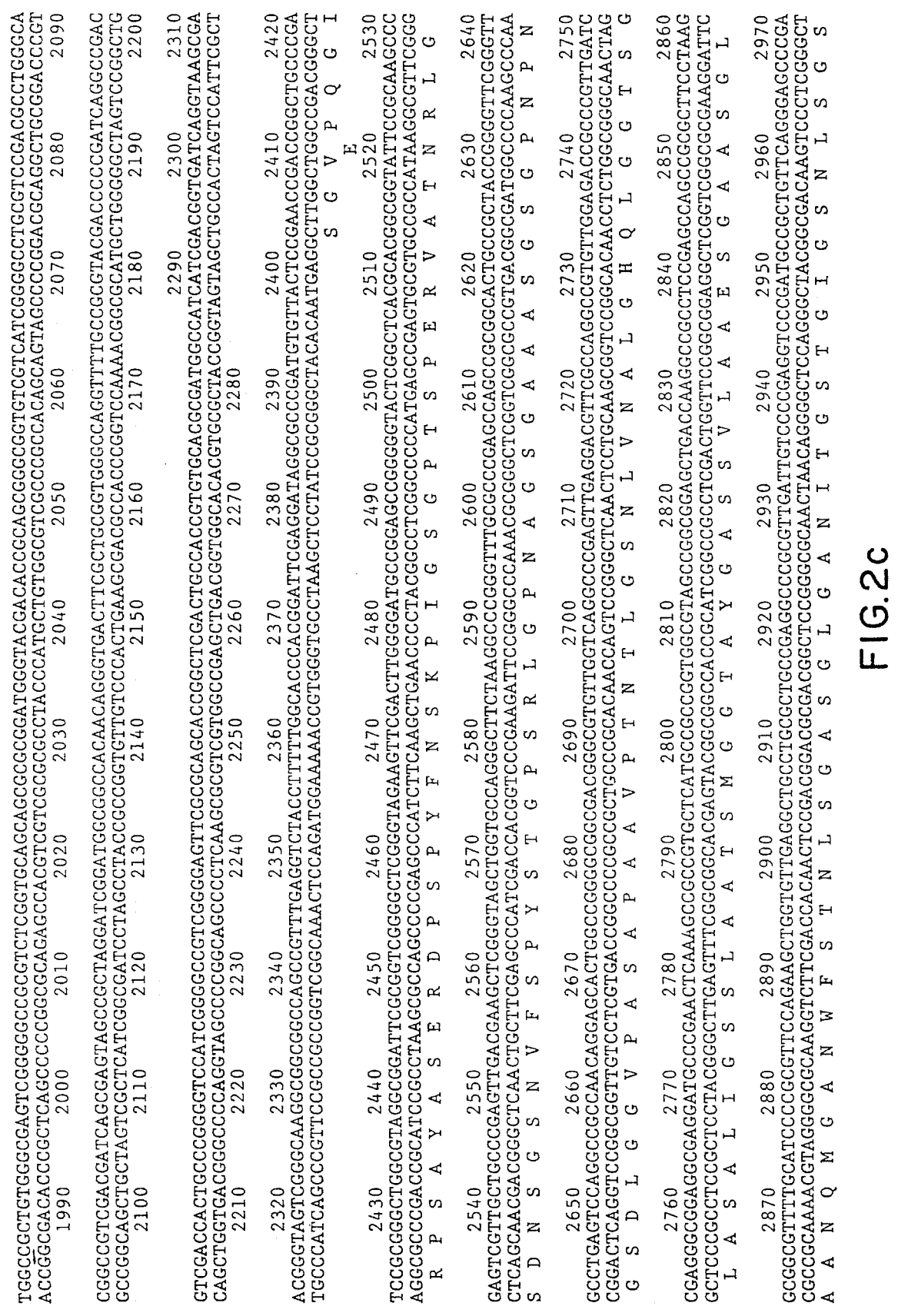
Figure 2D:
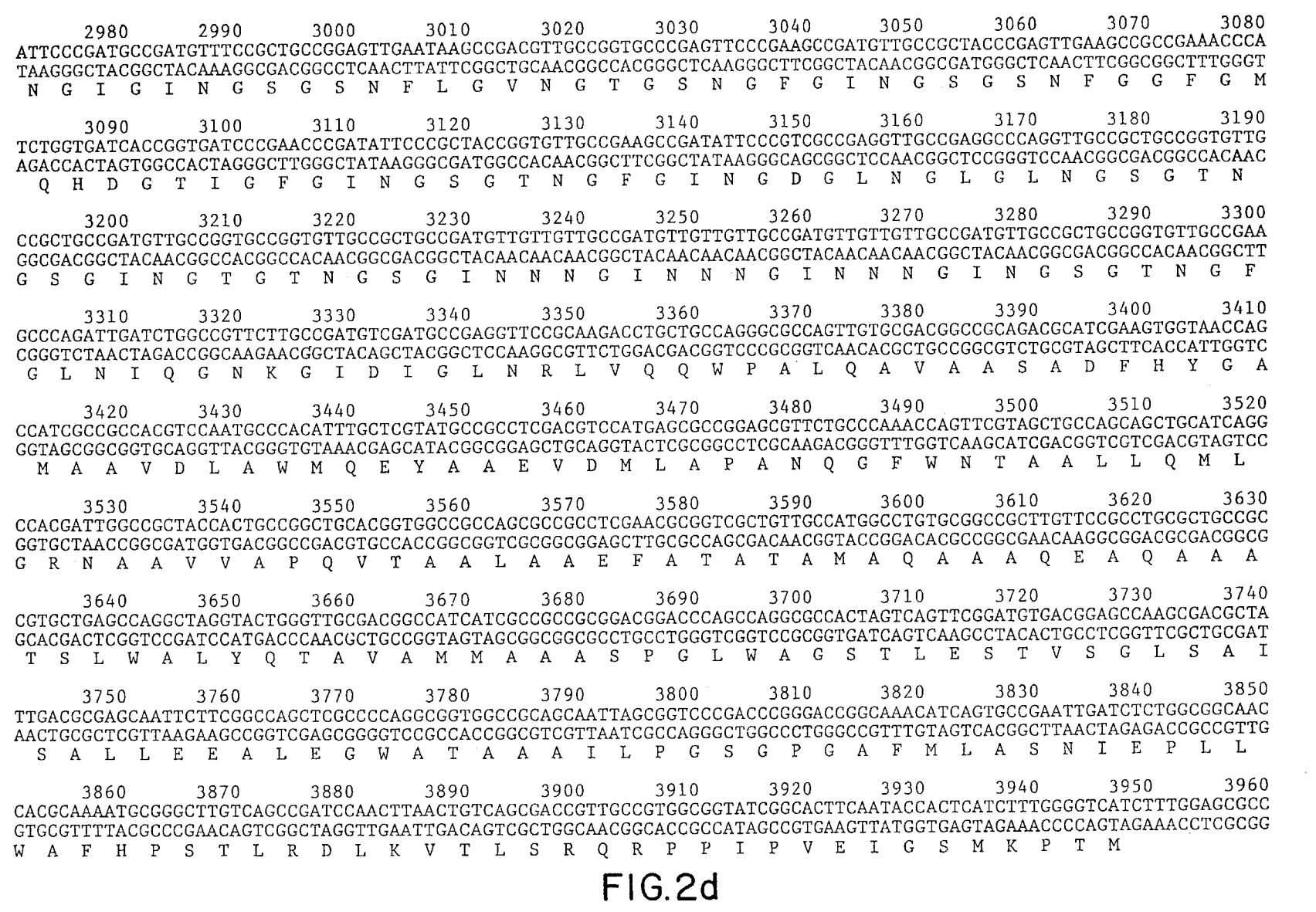

FIG. 2 shows the nucleotide sequence of the region containing the *M. tuberculosis* 65KD antigen and 517 protein genes, and is provided as four sheets labeled 2A, 2B, 2C and 2D. The deduced amino acid residue seqences of the two long open reading frames (ORFs) capable of coding for proteins containing 540 and 517 amino acid residues, respectively, are shown using the one letter code over (540) or under (517) the appropriate triplets. Asterisks above or below the respective sequences indicate the positions of stop codons (TGA, TAG or TAA) in the DNA sequences. Each sequence is shown as beginning with the first methionine (M) residue in phase with the ORF and downstream of the nearest upstream stop codon.

Figure 3:
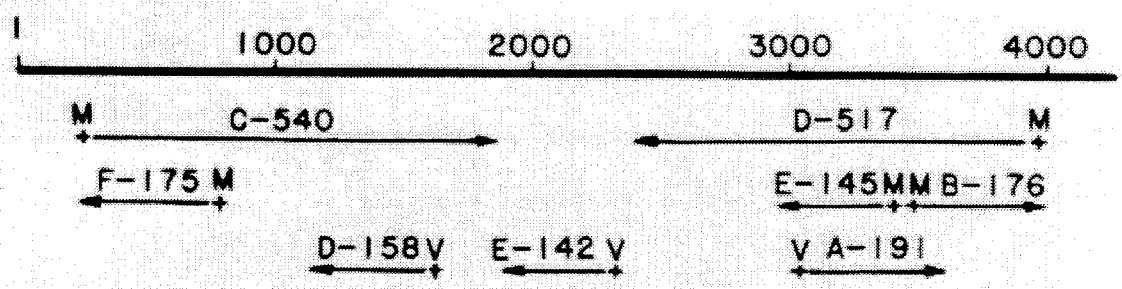

FIG. 3 is a schematic representation of the open reading frames found in the portion of the mycobacterial DNA sequence that codes for the 65KD antigen. The heavy line near the top of the Figure represents a portion of the genome that includes the 540 and 517 proteins. The shorter, arrow-tipped lines beneath the heavy line indicate DNA sequences that exceed 120 amino acid residues in length. Putative initiation triplets are identified on the shorter lines by the letter "M" (AUG) or the letter "V" (GUG) at the 5'-end of each open reading frame in the relatively shorter sequences illustrated beneath the heavy line. Arrows indicate the coding direction.

Figure 4A:
Figure 4B:
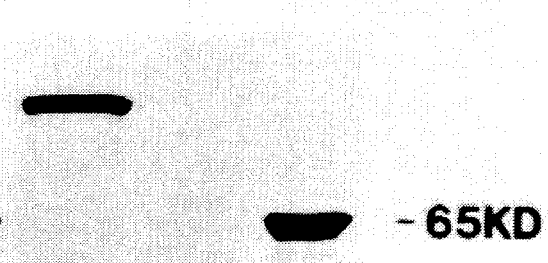

FIG. 4 is a photograph of a Western blot analysis of products of the 540 amino acid residue open reading frame, and contains two panels, A and B. Cells were grown and induced (except for lane 2, Panel A) and crude extracts were prepared as described in the Materials and Methods section, hereinafter. For each lane, except lane 5,200 micrograms (ug) of protein were electrophoresed on a 10% Laemmli gel, and transferred to nitrocellulose. For lane 5, 500 ug of protein were loaded. The immobilized proteins were reacted with the IT-13 antibodies and visualized, as discussed hereinafter.

For Panel A, the proteins in the lanes were: lane 1, JM83; lane 2, JM83 (pTB22) uninduced; and lane 3, JM83 (pTB22) induced with IPTG. For Panel B, the proteins in the lanes were: lane 1, JM83 (pTB12); lane 2, Y1089 (λSK116); lane 3, Y1089 (λRY3146); lane 4, BNN97 [*E. coli* C600 containing λgt11]; and lane 5, JM83 (pTB12).

DEFINITIONS

The following abbreviations and symbols are used herein.

bp—base pair(s)

kbp—1000 bp

KD—kilodalton(s)

M,—apparent relative molecular mass

DNA—deoxyribonucleic acid replicon—the unit that controls individual acts of replication; it has an origin at which replication is initiated and it can have a terminus at which replication stops.

When used in a context describing or depicting nucleotide sequences, the purine or pyrimidine bases forming the nucleotide sequence are depicted as follows:

A—deoxyadenyl

G—deoxyguanyl

C—deoxycytosyl

T—deoxythymidyl

In describing a nucleotide sequence each three-letter triplet constituted by the bases identified above represents a trinucleotide of DNA (a codon) having a 5'-end on the left and a 3'-end on the right of the upper sequence of FIG. 2, and a 5'-end on the right and a 3'-end on the left of the lower, complementary sequence.

The word "antigen" is often used in the art for an entity that is bound by an antibody. The word "immunogen" is often used in the same context for the entity that induces the production of antibodies. Where the antigen and immunogen are the same entity, both are often referred to an antigen.

The present invention deals with antigens and immunogens in the above context, which context typically relates to B cells and antibodies. Notwithstanding the B cell/antibody context, the present invention also contemplates T cells.

A more general definition of immunogen and antigen apply in the context of T cells and T cell stimulation. In that more general definition, an "antigen" is an entity acted upon by a component of the immune system, and an "immunogen" is an entity that initiates an immune system response. Where antigen and immunogen are the same, both are referred to as an antigen. An "immunologically active" entity interacts with antibodies or T cells, or can initiate a cellular or humoral immune response.

DETAILED DESCRIPTION OF THE INVENTION

I. OVERVIEW

In studies discussed hereinafter, the isolation of the gene encoding the *M. tuberculosis* 65KD antigen and the determination of its nucleotide sequence are reported. The sequence contains an open reading frame encoding 540 amino acid residues or about 60,000 daltons, which corresponds to the 65KD antigen. A second long open reading frame capable of encoding a protein of 517 amino acids was also found on the mycobacterial DNA fragment containing the 65KD antigen gene, adjacent to that gene. Interestingly, the central region of the deduced amino acid residue sequence of the 517 amino acid protein contains several tandemly arranged, perfect and imperfect repeats of a five amino acid residue sequence. This feature is reminiscent of the features of the sequence of the major T-cell antigen of the sporozoite stage of the human malarial parasite [Nussenzweig et al., (1985), *Cell*, 42:401–403].

II. RESULTS

A. Isolation and Analysis of Recombinants Expressing the 65KD Antigen

To isolate the gene that encodes the 65KD antigen, monoclonal hybridoma antibodies directed against this antigen were used to screen a protein expression library constructed with mycobacterial DNA. An expression library was chosen since it was not known *a priori* if the *M. tuberculosis* genes would be expressed in *E. coli*. Such a recombinant DNA library has been constructed by Young et al., (1985), *Proc. Natl. Acad. Sci. USA*, 82:2583–2587, and contains genomic DNA fragments of *M. tuberculosis* inserted into the expression site of the lambda-gt11 (λgt11) vector. In this system, the inserted coding sequences can be expressed as a fusion protein with beta-galactosidase. The 65KD antigen-specific monoclonal hybridoma antibodies used in these studies were generated in the laboratories of Dr. T. M. Buchanon (Pacific Medical Center, University of Washinton, Seattle Wash.) and Dr. J. Ivanyi (MRC Tuberculosis Unit, Hammersmith Hospital, London) and were obtained from the Steering Committee on the Immunology of Tuberculosis of the World Health Organization.

As the initial antibody probe, a pool containing three monoclonal antibodies directed against the 65KD antigen was used (IT-13, IT-31, and IT-33). Thirty-eight positive signals were detected in a screen of about $8 \times 10^5$ recombinant phage.

The phage corresponding to the positive signals were twice plaque purified and then assayed for reactivity with the individual antibodies. The results of that purification and assay are shown in Table 1, below.

TABLE 1

| Patterns of Antibody Reactivities[1] | | | |
| --- | --- | --- | --- |
| | Reactivity With Antibodies | | |
| Number of Clones | IT-13 | IT-31 | IT-33 |
| 28 | + | + | + |
| 3 | + | + | − |
| 3 | − | + | + |
| 2 | − | + | − |
| 2 | − | − | + |

[1]Recombinant clones expressing antigens reactive with the 65 KD antigen specific monoclonal antibodies IT-13, IT-31, and IT-33 were isolated as described in the text. For the initial screen, a pool of the three antibodies that contained a 1:1000 dilution of each antibody was used to screen a total of about $8 \times 10^5$ recombinant phage from the lambda gt11-*M. tuberculosis* library. To determine which monoclonal antibody reacted with which of the 38 plaque-purified recombinants, about 100 plaque-forming units (pfu) of each recombinant phage were inoculated in small spots on a lawn of *E. coli* Y1090. The phage were allowed to grow, and were induced to synthesize the foreign proteins as described herein. The filters were then reacted with a 1:1000 dilution of one of the monoclonal hybridoma antibodies as described in Materials and Methods.

Twenty-eight of the recombinants produced antigens that reacted with all three antibodies, whereas ten recombinants produced antigens that reacted with one or two of the antibodies. Overall, the patterns of reactivity indicate that although the three antibodies react with the same mycobacterial antigen, each recognizes a different epitope on that antigen. Richard A. Young (Whitehead Institute, M.I.T.) has also screened this λgt11-M. tuberculosis library with one of these antibodies (IT-13) and detected 10 additional recombinants [Young et al., (1985), *Proc. Natl. Acad. Sci. USA*, 82:2583–2587]. These recombinants were not assayed for reactivity with the other antibodies.

Figure 1:
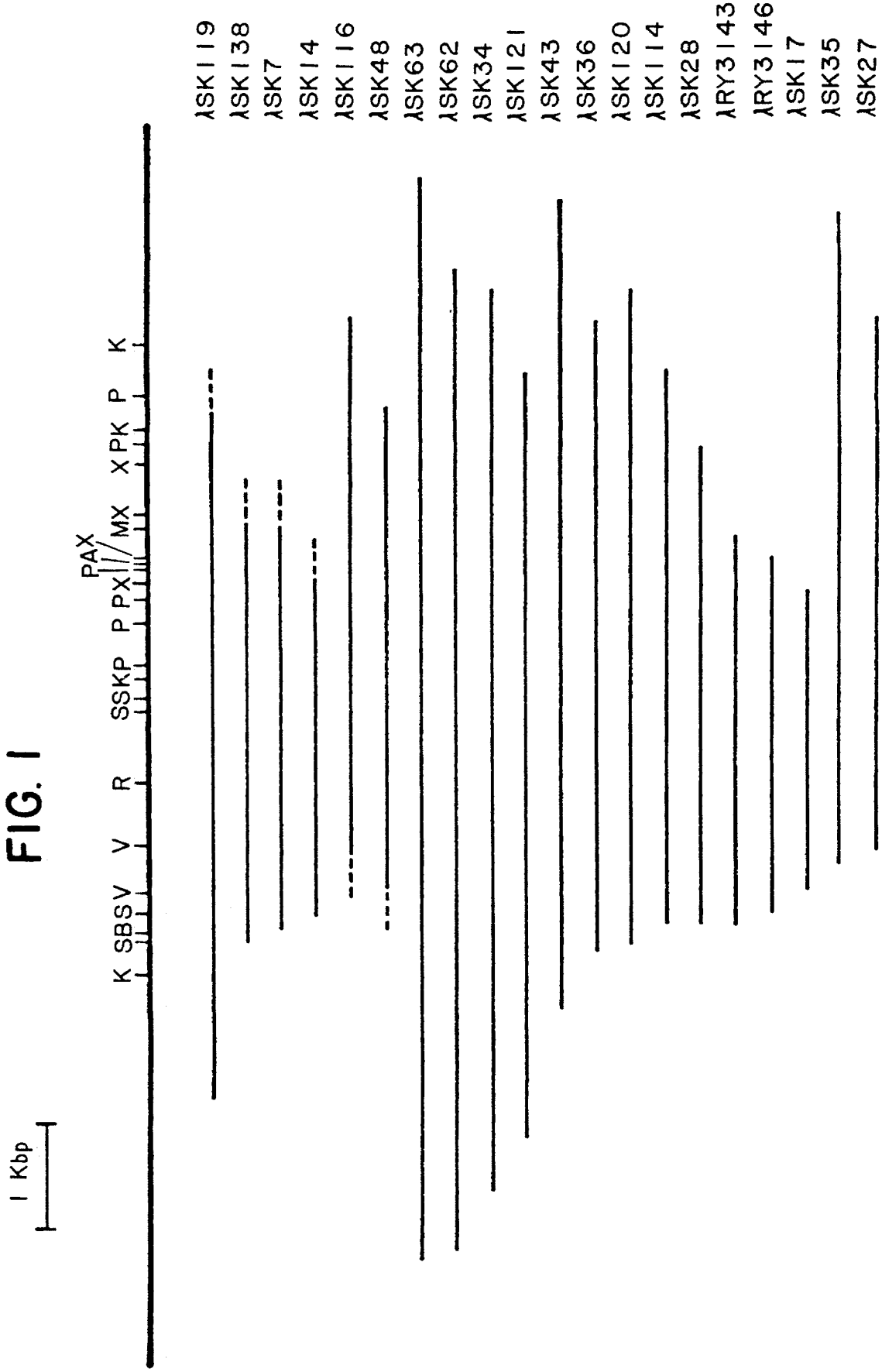
FIG. 1 is a schematic restriction map of recombinants expressing the *M. tuberculosis* 65KD antigen. The portion of the genome containing the 65KD protein is shown as the heavy line at the top of the Figure along with the relative positions (short perpendicular lines abutting the heavy line) of restriction endonuclease cleavage sites. The single letters adjacent those short lines are indicia of the endonclease that cleaves the genome at the indicated sites, and are: A=SacI, B=Bgl II, K=KpnI, M= BamHI, P=PstI, R=EcoRI, B=Sal I, V=PvuII, and X=XhoI.

DNA was isolated from twenty of the recombinants expressing the 65KD antigen and a restriction enzyme cleavage site map was deduced for this region of the mycobacterial genome (FIG. 1). In most of the recombinants, the mycobacterial DNA insert was flanked by EcoRI sites as expected from the way in which the library was constructed.

However, in 6 of the 20 recombinants studied, only one of the expected EcoRI sites was present. This observation raises the possibility that a significant fraction of the recombinant phage in this library might have arisen from the insertion of a fragment containing only one functional EcoRI site into the λgt11 EcoRI site or that some clones might have undergone some sort of recombination, rearrangement or deletion event during propagation that removed one of the EcoRI sites.

The deduced restriction map is in good agreement with the published map of the gene for the M. bovis 65KD antigen [Thole et al., (1985), Infect. Immun., 50:800–806] except for the presence of two additional SmaI sites in the M. tuberculosis gene. The map does not match well with that of the M. leprae 65KD antigen gene [Young et al., (1985), Nature, 316:450–452]. This is not unexpected given that based on DNA homology studies, M. tuberculosis is at least 90% homologous with M. bovis and only about 30% homologous with M. leprae, Athway et al., (1984), Int. J. Syst. Bacteriol., 34:371–375; Imaeda, (1985) Int. J. Syst. Bacteriol., 35:147–150.

To determine the nucleotide sequence of this region of the mycobacterial genome, several fragments from the λgt11 recombinants were subcloned into the plasmid vector pUC19. The majority of the sequence of this region was determined from a subclone (pTB7) of the 1.4 kilobase pair (kbp) EcoRI fragment of λSK7 and a subclone (pTB9) of the 2.6 kbp EcoRI fragment of λRY3143. The sequence across the EcoRI site at the junction of these two fragments was determined from a fragment isolated from a subclone (pTB11) of the 2.8 kbp KpnI fragment of λSK119. The sequence of the region 5' to the 2.5 kbp EcoRI fragment was determined from a subclone (pTB12) of the 2.4 kbp KpnI fragment of λSK119.

In all, the nucleotide sequence of 4380 base pairs of the mycobacterial DNA was determined by a combination of the Sanger dideoxy chain termination [Sanger et al., (1980), J. Mol. Biol., 143:161–178] and Maxam-Gilbert chemical degradation [Maxam et al., (1976), Proc. Natl. Acad. Sci. USA, 74:560–564] sequencing techniques. The sequence is shown in FIG. 2.

As expected for M. tuberculosis genomic DNA [Wayne et al., (1968), J. Bacteriol., 96:1916–1919], the base composition of this fragment was about 66% G+C. The high G+C content increased the chances of sequencing artifacts due to compressions, and made it imperative that the sequences were determined for both strands in all regions.

B. Open Reading Frames

The sequence contains five open reading frames (ORFs) that begin with an ATG triplet and contain greater than 120 amino acids. Two of these exceed 200 amino acids in length. One can encode 517 amino acids and the other 540 amino acids.

There are an additional three open reading frames of 140–190 amino acid residues in length that do not contain an initiation ATG triplet but do contain a GTG triplet. It is not known if a GTG triplet can function as a translation initiation triplet in mycobacteria. The locations of these eight open reading frames are shown schematically in FIG. 3. No portions of the deduced amino acid sequences of any of these open reading frames displayed any significant homologies with sequences in the Protein Sequence Database of the Protein Identification Resource.

It should be noted that although an open reading frame exceeding 100 amino acids would be considered to have a high probability of being expressed into protein in most bacteria, this may not be true for the mycobacteria. That is, given that the G+C content of the insert is about 66%, a translation termination triplet (TAA, TAG or TGA) would be expected to occur on average about once every 41 amino acids as compared to about once every 21 amino acids in a genome with a G+C content of 50%. Perhaps then, an open reading frame of as many as 150–200 amino acids might be due to the random distribution of termination triplets rather than signifying possible biologic importance. As such, only the two very long open reading frames that could encode proteins of 517 and 540 amino acid residues, respectively, are described herein.

C. The 540 Amino Acid Residue ORF Corresponds to the 65KD Antigen one of the long open reading frames begins with an ATG triplet at positions 252–254 of the DNA sequence and extends to a TGA triplet at positions 1872–1874. This ORF encodes 540 amino acids. To determine if this open reading frame corresponded to the gene for the 65KD antigen, the 1511 bp BamHI-KpnI fragment from pTB12 (residues 438–1948 of the sequence represented in FIG. 2), which contains the majority of this open reading frame, was inserted into BamHI-KpnI-cleaved pUC19. In this construct, denominated pTB22, the open reading frame is expressed using the lacZ transcription and translation initiation signals present in the pUC19 vector, and results in the production of a fusion protein containing 15 amino acid residues at the amino-terminus encoded by the lacZ gene of pUC19 followed by 478 amino acids of the mycobacterial open reading frame.

Crude extracts were prepared from cells containing this plasmid, and were tested for reactivity with 65KD antigen-specific antibodies in Western blot analyses. The reactivity with monoclonal antibody IT-13 is shown in panel A of FIG. 4. In all, five different monoclonal antibodies specific for the 65KD antigen reacted with a species in the crude extract that migrated with an apparent relative molecular mass ($M_r$) of about 55,000 daltons (lane 3).

No reactivity was seen in extracts of E. coli lacking the plasmid (lane 1). Furthermore, the expression of this fusion protein is inducible with isopropyl-beta-D-thiogalactopyranoside (IPTG) (compare lanes 2 and 3). Therefore, it is concluded that this long open reading frame encompassing residues 252–1871 encodes the M. tuberculosis 65KD antigen. The phrases "540 amino acid residue protein" "540 protein" "65KD protein" and "65KD protein antigen" are used interchangeably herein for the 65KD protein of M. tuberculosis.

In addition, the purified recombinant 65KD protein was used in Western blot analyses using serum from human patients known to be infected with M. tuberculosis. In preliminary studies, antisera from those patients immunoreacted with the purified recombinant protein.

Those studies illustrate the use of that natural or recombinant protein as an antigen in a diagnostic assay method for the presence of naturally occurring antibodies to the 65KD protein in the infected patients, and thus for the detection of a Mycobacterium tuberculosis infection in those patients. Similar results are obtained in a more usual solid phase assay such as are carried out in a microtiter plate where the recombinant 65KD protein is affixed to a solid phase matrix to form a solid phase support and patient serum is the source of antibodies to be assayed.

Solid phase assays whether carried out in a microtiter plate, a dipstick or as a Western blot all require the similar steps and constitute variants of each other. Each has a solid phase matrix (mirotiter plate well, stick surface or nitrocellulose) to which the purified natural or a recombinant 540 amino acid protein coded for by the genome of *M. tuberculosis* as antigen is affixed, usually by adsorption, to form the solid phase support. The assayed sample such as patient serum or cerebrospinal fluid (where evidence of tubucular meningitis is sought to be assayed) in liquid form is admixed with the solid phase support to form a solid-liquid phase admixture. That admixture is maintained under usual biological assay conditions (e.g. zero degrees C to about 40 degrees C) for a time period sufficient for any antibodies present in the assayed sample to immunoreact with and bind to the antigen of the solid phase support. The solid and liquid phases are separated as by rinsing. The presence of antibodies bound to the solid support is thereafter determined as with a labeled reagent that reacts with the bound human antibodies.

A labeled reagent that reacts with bound human antibodies present is admixed with the solid phase to form a second solid-liquid phase admixture. That second solid-liquid phase admixture is maintained for a time period sufficient for the labeled reagent to react with the bound human antibodies. The second solid-liquid phase admixture is separated as by rinsing, and the amount of label present is determined. An amount of label present above a background, control value indicates the presence of anti-65KD protein antibodies and thus an infection by *M. tuberculosis*.

The labeled reagent that reacts with the bound human antibodies is preferably a labeled preparation of xenogenic anti-human antibodies such as alkaline phosphatase-conjugated goat anti-human Ig antibodies that are available from Tago, Burlingame, Calif. The presence of the bound alkaline phosphatase is typically determined spectrophotometrically by measurement of the enzymatic hydrolysis of a substrate molecule such as p-nitrophenyl phosphate to p-nitrophenol. Other enzymes such as horseradish peroxidase and other label types such as radioactive elements like iodine 125 are also useful. *S. aureus* protein A linked to a label such as $^{125}I$ can also react with the bound human antibodies of the separated solid phases to detect their presence.

The above diagnostic assay method is typically carried out in a clinical setting using a kit. The kit comprises at least one package that contains a solid phase support having a purified 540 protein encoded by the *M. tuberculosis* genome that is from the mycobacterium or is a recombinant protein as discussed herein affixed as an antigen to a solid matrix such as a plastic microtiter plate or dipstick. One or more additional reagents such as the labeled reagent that reacts with solid phase-bound human antibodies, a substrate for the labeled reagent (where needed for the label), buffer salts in solution or dry form, and the like can also be present in separate packages in the kit.

D. The 65KD Antigen Gene is Expressed in *E. coli*

Because previous studies had shown that most mycobacterial genes were not expressed in *E. coli* using the mycobacterial transcription and translation signal sequences [Clark-Curtis et al., (1985), *J. Bacteriol.*, 161:1093–1102; and Thole et al., (1985), *Infect. Immun.*, 50:800–806] a protein expression library was used in the cloning studies. In the λgt11-*M. tuberculosis* library, the inserted mycobacterial coding sequences should be expressed as fusion proteins with beta-galactosidase [Young et al., (1983) *Proc. Natl. Acad. Sci. USA*, 82:2583–2587]. It was somewhat surprising to find that the open reading frame encoding the 65KD antigen did not extend to the 5'-end of the mycobacterial DNA insert in λSK119. This suggested that the 65KD antigen was being expressed using the mycobacterial transcription and translation signal sequences.

With respect to the previously described *E. coli* consensus signal sequences, the mycobacterial sequences 180–230 base pairs upstream of the presumed initiator ATG codon do display reasonable matches with the consensus sequences for the −35 (3/3 match with the highly conserved TTG) and −10 (4/6 match with TATAAT) regions of *E. coli* promoters [Rosenberg et al., (1979), *Ann. Rev. Genet.*, 13:319–353]. There is also a 5/5 match with the Shine-Dalgarno sequence [Shine et al., (1974), *Proc. Natl. Acad. Sci. USA*, 71:1342–1346] for a prokaryotic ribosome binding site (GGAGG) 13 base pairs upstream of the presumed initiator triplet for the 65KD antigen open reading frame. Although the precise locations of the mycobacterial regulatory sequences have not been determined experimentally, the results of the two studies described below suggest that the mycobacterial sequences are indeed functional in *E. coli*.

The size of the anti-65KD reactive material produced by the recombinants was determined in a Western blot assay. To do this, crude lysates of cells expressing recombinant plasmids or phage that had been shown to contain the entire 65KD antigen gene (λSK116, pTB12) as well as those that had been shown to contain a large portion of the 65KD antigen open reading frame fused to B-galactosidase (λRY3146; pTB22 that contains the 540 protein DNA from position 438 through position 1948 of FIG. 2) were prepared as described in the Materials and Methods section.

The lysates were electrophoresed on 10% Laemmli SDS-polyacrylamide gels, and the separated proteins were electrophoretically transferred to nitrocellulose. The SDS-denatured, immobilized proteins were then reacted with monoclonal antibodies specific for the 65KD antigen.

The results using antibody IT-13 are shown in FIG. 4. In cells expressing recombinants carrying the fused open reading frame, the monoclonal antibodies detected a single strongly reactive species migrating with an $M_r$ of about 160,000 daltons as well as occasionally detecting smaller species (FIG. 4, Panel B, lane 3). In another fused open reading frame recombinant, the monoclonal antibodies detected a single reactive species migrating with an $M_r$ of about 55,000 daltons (FIG. 4, Panel A, lane 3]. In the extracts of the cells expressing recombinants that contained the entire 65KD gene, the monoclonal antibodies detected a single strongly reactive species that migrated with an $M_r$ of about 64,000 daltons (FIG. 4, Panel B, lanes 1 and 2).

Smaller reacting species (about 40,000–55,000 daltons) were observed when large amounts of the extracts were loaded (lane 5) or when the protease inhibitor was omitted from the lysis buffer. Occasionally, a minor reacting species was also observed migrating with an $M_r$ of about 67,000 daltons.

Given the sizes of the anti-65KD-reactive materials, these data indicate that the 65KD antigen can be expressed using the mycobacterial translation initiation signals present in the 65KD gene. Also, since the vector contribution to the recombinant plasmids does not contain any known sequences that are properly located and oriented to promote the transcription of the inserted DNA, these data suggest that the mycobacterial transcription initiation signals function in *E. coli* to allow the expression of the 65KD antigen.

In order to obtain an approximate measure of the efficiency of utilization of the mycobacterial transcription and translation initiation signals in *E. coli*, two plasmids were constructed that placed the expression of enzymatically active beta-galactosidase under the control of either the mycobacterial signal sequences or the lac gene signal sequences present in the plasmid pUC19.

First, the 3000 bp BamHI fragment from pMC1871 that contains the coding sequences for amino acid residues 8–1021 of beta-galactosidase [Shapira et al., (1983), *Gene*, 25:71–82] was inserted into the BamHI site of pTB12 (residues 437–442 of the sequence presented in FIG. 2). The resulting 8.1 kbp plasmid (pTB27) contains an open reading frame that encodes a fusion protein with 63 amino acid residues derived from the 65KD antigen gene followed by 1014 amino acids of beta-galactosidase, and whose expression is under the control of the transcription and translation signal sequences present in the mycobacterial DNA. As expected, this construct expresses a protein of about 120,000 daltons that reacted with anti-beta-galactosidase antibodies in a Western blot assay.

Second, the 3000 bp BamHI fragment from pMC1871 was inserted into the BamHI site in the polylinker of pTB9 that contains a 2.4 kbp fragment of the 65KD antigen gene inserted in the EcoRI site of pUC19. The resulting 8.1 kbp plasmid (pTB28) contains an open reading frame that encodes a fusion protein with 15 amino acid residues derived from the pUC19 lacZ gene and polylinker sequences followed by the 1014 amino acid residues of beta-galactosidase and whose expression is under the control of the lac gene signal sequences present in pUC19.

Crude extracts of cells containing these plasmids were assayed for beta-galactosidase activity as previously described. In cells containing pTB27, beta-galactosidase activity [about 2800 units/microgram (ug) protein] was about one-fourth that (11,000 units/ug protein) found in IPTG-induced cells containing pTB28. Given the unknowns inherent in this study (e.g., the specific activities and relative stabilities of the two fusion proteins), one cannot make a precise quantitative statement about the relative strengths of the mycobacterial signal sequences and the *E. coli* lac gene signal sequences based on the relative enzymatic activities found in the two cell extracts. However, the data do indicate that these mycobacterial transcription and translation signal sequences are efficiently recognized in *E. coli*.

E. The 65KD Antigen Sequence

Several interesting features of this long open reading frame have been revealed by a computer-aided analysis of the sequence. The overall base composition of this open reading frame is 65.5% G+C. However, the G+C content varies considerably within the codons such that the G+C content of the bases occupying the first two residues of the codons is 55% while it is 87% for the bases found in the third position of the codons; thereby producing a bias towards using codons that have a G or C in the third position.

For example, 50 of the 51 leucine codons (CTX) have a G or C in the third position. Interestingly, the essentially random occurence of any of the four bases in the first two positions of a codon plus the preference for G or C in the third position of a codon is one strategy that allows an organism to have a high G+C content without limiting access to the amino acids whose codons contain A or T residues in the first two positions.

Although the deduced amino acid residue sequence of the 65KD antigen is particularly rich in alanine, glycine, leucine, and valine residues, the overall amino acid residue composition contains 52% hydrophobic and 48% hydrophilic residues. Computer-aided analysis of the alpha helical content Chou et al., (1978), *Adv. Enzym.*, 4.7:45–148 and hydrophobicity [Hopp et al., (1981), *Proc. Natl. Acad. Sci. USA*, 78:3824–3828] of the amino acid residue sequence revealed numerous regions that could participate in alpha helical structures and no extended regions of high hydrophobicity. These data suggest that the 65KD antigen is not an integral membrane protein but rather its sequence resembles that of a soluble protein.

As discussed before, the 65KD antigen appears to be a major T cell immunogen and antigen in man. It has been suggested that immunodominant T cell epitopes are short stretches of amino acids that can form amphiphilic helices where one side of the helix is hydrophobic and the other side hydrophilic, Berzofsky, (1985), *Science*, 229:932–940. Based on computer modeling, seven stretches of amino acids within the sequence of the 65KD antigen have been identified that could form such amphiphilic helices. A list of those peptides is shown in Table 2, below.

TABLE 2

| Residue Positions[1] | Sequence[2] | | | | | | | | | | | | | | | | | |
|---|---|---|---|---|---|---|---|---|---|---|---|---|---|---|---|---|---|---|
| 11–28 (58) | A | R | R | G | L | E | R | G | L | N | A | L | A | D | A | V | K | V |
| 66–79 (59) | E | K | I | G | A | E | L | V | K | E | V | A | K | K | | | | |
| 114–130 (60) | G | L | K | R | G | I | E | K | A | V | E | K | V | T | E | T | L | |
| 154–172 (61) | Q | S | I | G | D | L | I | A | E | A | M | D | K | V | G | N | E | G | V |
| 219–233 (23) | L | L | V | S | S | K | V | S | T | V | K | D | L | L | P | | | |
| 394–408 (62) | I | E | D | A | V | R | N | A | K | A | A | V | E | E | G | | | |
| 494–508 (63) | V | K | V | T | R | S | A | L | Q | N | A | A | S | I | A | | | |

[1]Residue positions are denominated using the one letter amino residue sequence of the 65 KD protein shown in FIG. 2 that depicts the methionine residue coded for by the triplet beginning at base pair position 252 as the first residue of the protein. Parenthesized numbers refer to peptide numbers that begin with peptide number 1 shown in Table 4.
[2]These amino acid sequences are shown from left to right and in the direction from amino-terminus to carboxy-terminus, as is customary in the art.

F. DCH Assay With A Recombinant 65KD Protein

Exemplary delayed cutaneous hypersensitivity (DCH) assays were carried out using illustrative recombinant proteins described herein as test antigens after immunization with *M. tuberculosis, M. bovis* or saline. These assays were carried out following the procedure described in Minden et al. (1986) *Infec. Immun.* 53:560–564.

Briefly, the mammalian hosts were immunized with a sufficient amount of *M. tuberculosis* or *M. bovis* to induce an immunological response, or with a control (saline). After maintaining the animals for a time period sufficient for the initial immunological response to the immunogen to subside, the animals were challenged by intradermal injection with inocula containing the 65KD protein, a recombinant 65KD protein, or a recombinant fusion protein that contained the 65KD protein as the test antigen dissolved or dispersed in a physiologically tolerable diluent, or with a control. The test antigens were present in an amount sufficient to induce erythema and induration at the site of administration in a mammal previously immunized with *M. tuberculosis* or *M. bovis*.

The results of this study are shown in Table 3, below.

TABLE 3

| | DCH Assays With Recombinant Antigens No. Positive/No. Assayed Of Guinea Pigs Immunized With[2]: | | |
|---|---|---|---|
| Challenge Antigen[1] | *M. tuberculosis* | *M. bovis* | Saline |
| Saline (0) | 0/5 | 0/5 | 0/5 |
| BNN97[3] (10) | 0/5 | 0/5 | 0/5 |
| λ1089[4] (10) | 5/5 | 5/5 | 0/5 |
| λ1089[4] (1) | 5/5 | 5/5 | 0/5 |
| pTB22[5] (10) | 5/5 | 5/5 | 0/5 |
| pTB22[5] (1) | 5/5 | 5/5 | 0/5 |
| BCG-S[6] (1) | 5/5 | 5/5 | 0/5 |
| PPd[7](5 T.U.) | 5/5 | 5/5 | 0/5 |

[1]Challenge antigen compositions were injected intradermally as discussed in Materials and Methods using amounts of 1 or 10 ug/100 ul per injection as indicated by the parenthesized numeral after each antigen, except for purified protein derivative (PPd) that was used in an amount of 5 tuberculin units (T.U.).
[2]The number of guinea pigs exhibiting positive DCH responses is in the numerator, whereas the number of guinea pigs assayed is in the denominator. The immunization protocol is described in Materials and Methods.
[3]BNN97 was a crude lysate prepared from λgt11-infected *E. coli.* The crude lysate was partially purified by ammonium sulfate precipitation as described in the Materials and Methods section.
[4]λ1089 was a crude lysate prepared from λSK119-infected *E. coli* that expressed the 65 KD antigen. The crude lysate was partially purified by ammonium sulfate precipitation as described in the Materials and Methods section.
[5]pTB22 was a crude lysate prepared from *E. coli* containing pTB22 that expressed the 65 KD antigen as a fusion protein that contained a portion of the beta-galactosidase molecule and about the carboxy-terminal 88 percent of the 65 KD protein. The crude lysate was partially purified by ammonium sulfate precipitation as described in the Materials and Methods section.
[6]BCG-S was an extract of *M. tuberculosis* prepared as described in the Materials and Methods section.
[7]PPd was obtained from Connaught Laboratories, Ltd., Willowdale, Ontario, Canada.

As can be seen from the above results, the 65KD protein coded for by the DNA sequence of FIG. 2 can be utilized in DCH as part of a method to determine whether a mammalian host such as guinea pig had previous immunolgical exposure to *M. tuberculosis* since the T leucocytes of the host animals produced erythema and induration at the sites of administration in the animals previously immunized with *M. tuberculosis* and *M. bovis*, and produced no reactions in the saline-immunized animals. Those results also show that recombinant 65KD protein molecules are similarly useful.

Recombinant fusion proteins that contain a portion of the beta-galactosidase molecule peptide-bonded to the amino-terminus of the 65KD protein are also useful, as are fusion proteins that contain a portion of the beta-galactosidase molecule and an immunologically active portion, about the carboxy-terminal 85% of the 65KD protein, e.g., the protein expressed by pTB22. Fusion proteins that contain one or more peptide sequences as are described in Tables 2 and 4 hereinafter are also useful. The phrase "previous immunological exposure" and its grammatical variants is used herein to mean that the mammalian host had been immunized or infected by one of the mycobacteria and the host mammal mounted an immune response (primary response) to the immunogens provided by the mycobacteria, and that that immune response had subsided.

G. The 517 Amino Acid Protein

1. The Open Reading Frame

A second long open reading frame begins with an ATG codon at positions 3948–3946 of FIG. 2 and extends to a TAA triplet at positions 2397–2395 on the DNA strand complementary to the DNA strand encoding the 65KD antigen, thereby making those open reading frames adjacent in the genome. This open reading frame can encode a protein that contains a sequence of 517 amino acid residues, and that protein is referred to herein as the "517 amino acid protein" or the "517 protein". The 517 protein coding region thus extends from position 3948 through position 2398 of FIG. 2.

Given that the two long open reading frames are located adjacent and downstream from each other on the complementary strands, one might expect that the transcription of one gene might interfere with the transcription of the other unless there were transcription termination signals within the intergenic region. Indeed, there are several short sequences (e.g., 2134–2160) within the 520 base pair intergenic region that have features reminiscient of the transcription termination signals of gram-negative bacteria [Rosenberg et al., (1979), *Ann. Rev. Genet.,* 13:319–353]. That is, regions containing short, G+C-rich, inverted repeats capable of forming stem and loop structures followed by a stretch of three or more T residues about 20 bases from the center of dyad symmetry. Perhaps these inverted repeats might function as transcription termination signals to allow the independent expression of each of these mycobacterial genes.

To determine if the 517 amino acid open reading frame was expressed into protein in *E. coli*, extracts of cells containing a plasmid (pTB11) carrying the complete open reading frame were probed with a polyclonal rabbit antiserum elicited with a sonicated extract of *M. tuberculosis* bacteria in a Western blot assay. In these recombinants, the putative protein product of the 517 amino acid open reading frame would have to be expressed using the mycobacterial regulatory sequences. The polyclonal antiserum detected more than 100 species in an extract of *M. tuberculosis* cells as well as the 65KD antigen in extracts of *E. coli* cells carrying the appropriate plasmid (pTBI? ), but did not detect any novel proteins in extracts of *E. coli* cells containing plasmids carrying the 517 amino acid residue protein open reading frame. Hence, either this open reading frame is not expressed in *E. coli* using the mycobacterial regulatory sequences or the particular antiserum used in the immunoblots did not contain antibodies directed against this protein.

It is not surprising that this open reading frame is not expressed in *E. coli* using the before-discussed recombinant since previous studies suggest that most mycobacterial genes are not expressed in *E. coli* [Clark-Curtiss et al., (1985), J. Bacteriol., 161:1093–1102; and Thole et al., (1985), Infect. Immun., 50–800–806]. Also, this open reading frame does not contain any impressive matches to the *E. coli* consensus promoter sequences within the 400 bases upstream of the ATG triplet although it does contain a 3/5 match with the Shine-Dalgarno consensus sequence for ribosome binding sites 12 bases upstream of the initiator ATG triplet. Nonetheless, given the size of this open reading frame and its unique structural features (discussed below), it most likely is expressed into protein in *M. tuberculosis* and can be expressed in *E. coli* using a recombinant vector designed for that expression, as is discussed hereinafter.

2. Structural Features of the 517 Protein

The second long open reading frame could encode 517 amino acids or a protein of about 51,000 daltons (calculated M.W.=50,561). The deduced amino acid residue sequence is rich in alanine, asparagine, glycine, and serine and overall is composed of 54% hydrophobic residues and 46% hydrophilic residues. The amino acid sequence of this protein does not display significant homologies with any of the protein sequences in the Protein Database.

The most striking features of this sequence occur between amino acid residues 500 and 350, and more particularly at positions 217 through 328. This region contains many repeats of short stretches of amino acids.

For example, the five amino acid sequence asparagine-asparagine-asparagine-isoleucineglycine (N N N I G, using one letter code) is repeated three times consecutively at positons 227 through 241.

But perhaps the most interesting feature concerns a five amino residue sequence that displays at least partial matches with several sequences in this region. These five residue sequence repeats begin at position 217 and continue through position 328 of FIG. 2. The consensus sequence of this repeat appears to be X—glycine—asparagine—Z—glycine, or XGNZG, using one letter code. For the fifteen sequences that match this consensus sequence, X is most often phenylalanine, serine or threonine (12/15), although X can also be isoleucine, leucine and aspattic acid. Z is most often isoleucine or threonine (10/15), but is also sometimes serine, leucine or valine. Additional sequences between positions 200 and 350 display partial matches with the consensus sequence (i.e., match 2 of the 3 core residues).

The above five residue sequences are arranged, from the amino-terminus toward the carboxy-terminus, with two abutting (contiguous) XGNZG sequences that are contiguous with the three NNNIG sequences that are themselves contiguous to eight contiguous XGNZG sequences. A gap of about seventeen residues follows, that is itself followed by three contiguous XGNZG consensus sequences. Another gap of five residues ensues that abuts another two contiguous five residue XGNZG consensus sequences. Interestingly, both of those gaps contain sequences having two of the three core residues of the consensus sequence, as well as properly spaced X and Z residues.

It is further noted that this region contains a direct repeat of a fourteen amino acid residue sequence with only one mismatch (residues 295–308 and 315–328). Those sequences are shown below using one letter code:

| 295–308 | F | N | S | G | S | G | N | I | G | F | G | N | S | G |
|---|---|---|---|---|---|---|---|---|---|---|---|---|---|---|
| 315–328 | F | N | S | G | S | G | N | I | G | I | G | N | S | G. |

As expected, since the amino acid residue repeats of the consensus sequences are not exact, the nucleotide sequences in this region are not exact repeats. This observation suggests that recombinational processes such as an unequal crossing over may not play a role in causing rapid evolutionary changes in this region as is often observed for highly repeated nucleotide sequences.

The remainder of this protein sequence does not display any other particularly striking features.

The highly repetitious nature of the 517 residue protein is reminiscent of the repeated structures found in the major coat proteins of the sporozoite stage of the malaria parasite [Nussenzweig et al., (1985), *Cell*, 42:401–403]. These circumsporozoite or CS proteins are 40–60 KD proteins located on the membrane of the infectious sporozoite and contain a strongly immunodominant epitope that reacts with most of the anti-sporozoite antibodies found in polyclonal antisera as well as all of the monoclonal antibodies raised against the sporozoite stage. The central region of these proteins contains 20–40 tandemly arranged repeats of a 11–12 amino acid sequence.

In *Plasmodium falciparum*, the immunodominant epitope is contained within three consecutive repeats of the sequence asparagine-alanine-asparagine-proline (NANP; which is repeated 37 times in one isolate) and antibodies directed against this 12-residue repeat can provide immunologic protection against infection with the malaria parasite. The sequence of the repeat differs in the various species of this parasite and the number of repeats can vary within different isolates of the same species. The similarity of the repeated nature of the CS protein and that of the 517 amino acid residue *M. tuberculosis* protein raises the interesting possibility that the repeated sequences in the 517 residue protein might play some role in the immune response to mycobacteria.

3. Expression of the 517 Protein

Although the 517 protein was not expressed using the before-described recombinant construct, that protein was expressed in *E. coli* using a recombinant expression vector designed specifically for its expression. That recombinant expression vector was constructed as follows, using the base pair numbering of FIG. 2. It is to be understood that the DNA sequence of interest here is that shown in the lower of the two DNA sequences depicted, and that sequence, is read from right to left and in the direction from 5'-end to 3'-end, although the sequence position numbers are read from left to right and in the direction from 5'-end to 3'-end for the upper sequence.

The double stranded DNA sequence of FIG. 2 was cleaved with endonuclease PvuII to provide a fragment that extends from position 3511 to position 4019 (509bp). That fragment was ligated into the SmaI site of the pUC19 vector to form intermediate I. Two orientations were possible for ligation of the PvuII fragment in the vector. Proper orientation was determined by usual methods such as isolation of several insert-containing clones and preparation of restriction maps of the DNA from those clones. For example, a BglI fragment from a clone having the PvuII DNA fragment in the proper orientation contains about 1500 bp, whereas a BglI fragment from a clone having an improperly oriented PvuII fragment contains only about 1300 bp. Intermediate I was introduced into *E. coli* to propagate the vector DNA.

The propagated DNA of intermediate I was thereafter cleaved with endonucleases NotI (position 3603) and SalI (in the pUC19 polylinker site). The resulting NotI-SalI fragment was discarded, whereas the remainder of the DNA of Intermediate I was retained.

A further sample of the DNA sequence of FIG. 2 was cleaved with endonucleases NotI (position 3603) and SalI (position 2202) to provide a NotI-SalI fragment that was ligated into the appropriate sites of the retained Intermediate I DNA to form a second pUC19-derived vector denominated Intermediate II. That vector contained the complete 517 protein DNA sequence, and was propagated further in *E. coli*.

The propagated DNA of Intermediate II was collected and cleaved with endonucleases EcoRI and HindIII at their respective sites in the 517 protein gene and in the polylinker of pUC19. The resulting EcoRI-Hind III fragment that contained the 517 protein DNA was thereafter collected and ligated into those respective sites in the polylinker of plasmid vector pKK223-3 to form Intermediate III that contained the carboxy-terminal portion of the gene. Intermediate III was cloned in *E. coli* JM105. (pKK223-3 and JM105 are available from Pharmacia Fine Chemicals, Piscataway, N.J.)

A further sample of the DNA of Intermediate II was cleaved with EcoRI alone to excise a portion of that DNA from a position in the polylinker to position 2969 in the 517 protein. The resulting EcoRI fragment containing DNA that codes for the amino-terminal portion of the 517 protein was collected, and was thereafter ligated into the single EcoRI site of Intermediate III to form the expression vector that contains the entire 517 protein gene. That vector was also cultured in *E. coli* JM105 as a replication/expression medium.

It is noted that two orientations were possible for ligation of the EcoRI fragment in the expression vector. Proper orientation was determined by usual methods such as isolation of several insert-containing clones and preparation of restriction maps of the DNA from those clones. For example, a KpnI-HindIII fragment from a clone having the EcoRI DNA fragment in the proper orientation contains about 2000 bp, whereas a KpnI-HindIII fragment from a clone having an improperly oriented EcoRI fragment contains only about 800 bp.

Expression of a recombinant protein from vector pKK223-3 is inducible with IPTG, and the induced recombinant protein is expressed as the protein itself, and not as a fusion product. The resulting *E. coli* cells were thus grown and then induced with IPTG, as discussed elsewhere herein.

The expressed protein was produced in a relatively large amount and could be readily identified in an SDS-PAGE gel from a lysate of the *E. coli* cells. The 517 protein had an apparent $M_r$ of about 55,000 daltons in SDS-PAGE, as expected.

The expressed 517 protein can also be collected and purified, as with an affinity column made from Sepharose 4B (Pharmacia) to which antibodies raised to one or more of the 517 protein-related peptides are bound via the cyanogen bromide activation technique, or by ammonium sulfate precipitation, followed by DEAE-cellulose chromatography.

H. Recombinants and Vectors

The present invention thus contemplates the purified recombinant 540 protein and 517 protein, as well as those recombinant fusion proteins that also include all or a portion of another molecule such as beta-galactosidase fused to the amino-terminus of those proteins. Each of those recombinant proteins is useful for inducing the production of antibodies that immunoreact with those respective molecules as obtained from *M. tuberculosis* itself or from cells infected with that mycobacterium. Methods of preparing such antibodies are well known in the art and are similar to the methods utilized for the peptides of this invention as described hereinafter.

The purified recombinant 540 amino acid residue protein or its fusion proteins when present in an effective amount in an inoculum are also useful in a DCH assay, as described before. Those proteins are also useful in diagnostic methods and kits useful for assaying for the presence of infection by *M. tuberculosis*.

Nucleotide sequences are also contemplated, as are non-chromosomal plasmid vectors useful for propagating those DNA sequences and expressing the protein products coded for by those sequences.

A nucleotide sequence of this invention consists essentially of one of the before-described sequences. Thus, a nucleotide sequence of the invention excludes additional nucleotides that affect the basic and novel characteristics of a nucleotide sequence that codes for the 540 protein or the 517 protein.

A nucleotide sequence of the invention can include one or more transcriptional promoter sequences operationally linked to the sequence adjacent to the 5'-end thereof. Where translation of the DNA and protein expression are desired, the DNA also includes a translation initiating codon (ATG) and a translation terminating codon (TAA or TAG or TGA), each operationally linked adjacent to the 5'-end and 3'-end, respectively, of the sequence, with the translation initiating codon being located between the promoter sequence and the 5'-end.

A DNA sequence that codes for all or a portion of another molecule can also be included in the DNA molecule so that the translated (expressed) proteinaceous molecule is a fusion protein that includes an amino acid residue sequence of all or a portion of that other molecule fused (linked by a peptide bond) to the expressed 540 protein or 517 protein. An exemplary fusion polypeptide is the fusion protein molecule discussed herein that contains a portion of the beta-glactosidase molecule fused to the amino-terminus of the 540 amino acid residue protein.

All of the nucleotide sequences shown in FIG. 2 can be present so long as an enumerated DNA molecule remains replicable, where only replication is desired. Where replication and translation (proteinaceous molecule expression) are desired, those nucleotide sequences are present so long as the DNA molecule remains replicahie and the proteinaceous molecule containing the amino acid residue sequence of 540 protein or 517 protein expressed exhibits immunological cross-reactivity with the antibodies raised to an appropriate peptide described herein. In more preferred practice, only those base pairs needed for expression of a desired protein are utilized.

A non-chromosomal, plasmid vector for propagation and expression of a desired DNA nucleotide sequence as defined herein in a replication/expression medium, e.g., a unicellular organism or the like such as *E. coli*, *S. cerevisiae* or mammalian cells such as COS cells, is also contemplated. That vector comprises a replicon that is compatible with the replication/expression medium and contains therein the foreign DNA molecule (e.g., all or a portion of the sequence shown in FIG. 2) to be replicated in a manner such that the vector can propagate the DNA molecule.

In addition, the non-chromosomal plasmid vector also includes those sequence components that are utilized for transcription and translation. To that end, a transcriptional promoter can be operationally linked to the DNA molecule present adjacent to the 5'-end thereof, as already noted. The transcriptional promoter can be endogenous to the vector or exogenous to the vector. A transcriptional promoter endogenous to the vector such as the lac Z promoter-operator utilized in the vectors derived from pUC19 or the trp-lac (taq) promoter of pKK223-3 is preferred. A translational terminator can also be operationally linked adjacent to the 3'-end of the DNA molecule in some instances, although the nucleotide sequence represented by the formula of FIG. 2 contains such terminator sequences.

An initiation codon (ATG) adjacent to the 5'-end of the sequence that begins translation in a replication/expression medium is also required to be present in a vector used for expression. Such a codon can be present in a defined DNA molecule in frame, as is the case with the sequences shown in FIG. 2, or can be a portion of the precursor plasmid vector nucleotide sequence.

The before-discussed transcription promoter, translation initiating and translation terminating codons are frequently parts of the non-chromosomal plasmid vector as compared to a DNA molecule of the invention. For use in expression of the proteinaceous molecule, the precursor plasmid frequently also includes a ribosome binding site (Shine-Delgardo sequence) adjacent to the 5'-end of the foreign DNA molecule and located upstream from the initiation codon, as is well known. The vector's promoter such as the lacZ and tac promoters utilized herein typically contain a ribosome binding site.

Thus, the nucleotide sequence of the plasmid vector used for expression, aside from those nucleotides needed for the replication and general vector function include, in frame and from 5'-end to 3'-end, a ribosome binding site operationally linked adjacent to the 5'-end of a transcription promoter; that promoter operationally linked to the 5'-end of the translation initiating codon; that codon operationally linked to the 5'-end of: (a) a sequence of a portion of another molecule that is expressed as a fusion protein with the desired protein, or (b) a foreign DNA molecule of this invention; where (b) is present, that sequence is operationally linked to the 5-end of a DNA molecule of this invention. An expression vector containing the foreign DNA molecule of this invention, (however linked adjacent to its 5'-end) also contains a translation terminating codon adjacent the 3'-end of the foreign DNA.

It is to be understood that all of the DNA sequences of the vector must be compatible with the replication/expression medium utilized for replicating the DNA, and more preferably for expressing a product coded for (encoded by) a DNA molecule of this invention.

It is also to be understood that the before-recited signal sequences of the useful vector can be supplied to that vector by the foreign DNA or by a precursor to the final vector. For example, the translation initiation and termination codons in the expression vector for the 517 protein are provided by the foreign DNA, whereas the promoter and ribosomal binding site sequences are provided by the precursor plasmid.

A vector of the invention is at least capable of replicating (propagating) a DNA molecule of the invention. More preferably, the vector is capable of not only replicating a DNA molecule, but is also capable of expressing or translating the genomic information of that DNA into a recombinant protein molecule that is immunologically similar to the 540 protein or the 517 protein; i.e., will induce cross-reactive antibodies.

A non-chromosomal plasmid vector of this invention need not be limited to those vectors useful for replication and translation (expression) in *E. coli* as host replication/expression medium. Substantially any vector useful for replicating (propagating) and expressing a DNA sequence can be utilized for replicating the DNA, e.g. in mammalian or eukaryotic cells.

A wide range of such vectors is commercially available as are appropriate host replication media. Exemplary vectors, both plasmids and bacteriophages and hosts are available from the American Type Culture Collection of Rockville, Md., and are listed in its *CATALOGUE OF BACTERIA, PHAGES AND rDNA VECTORS*, sixteenth ed., 1985. In addition, plasmids, cosmids and cloning vectors are listed as being available in catalogues from Boehringer Mannheim Biochemicals of Indianapolis, Ind.; Bethesda Research Laboratories, Inc. of Gaethersberg, MD, and New England Biolabs, Inc. of Beverly, Mass.

I. Peptides

Another aspect of the present invention relates to a peptide that consists essentially of an amino acid residue sequence that corresponds substantially to a portion of the 540 or the 517 protein sequence. Such a peptide contains 5 to about 40 amino acid residues, and more preferably about 10 to about 20 amino acid residues that correspond substantially in sequence to a protein of either the 540 amino acid residue protein or the 517 amino acid residue protein that are coded for by the DNA sequence shown in FIG. 2.

A useful peptide most preferably contains only those amino acid residues that are identical or homologous to (conservative substitutions for) residues present in a sequence of either of the two above proteins. Additional residues of substantially any length can also be present at either or both termini of the peptide. However, any additional residues must not interfere with the activity of the peptide, as discussed hereinafter, and therefore, a peptide of this invention is said to "consist essentially" of an enumerated sequence. For example, a peptide of the invention is free of immunosuppressing sequences. In addition, if additional residues are present, and together with an above peptide correspond substantially in sequence to further portions of the same protein to which the sequence of the peptide substantially corresponds, the resulting peptide is of a molecular weight less than that of the naturally occurring 540 or 517 proteins, respectively.

A peptide of this invention is useful, inter alia, for inducing the production of antibodies in a laboratory mammal such as a mouse or rabbit. Those induced antibodies immunoreact with the inducing peptide as well as with the protein to which the peptide sequence substantially corresponds when that protein is in an SDS-denatured form as in a Western blot analysis subsequent to SDS-PAGE analysis.

Thus, the anti-peptide antibodies can be used in solid phase assays for the detection of the presence of an antigen that is the 540 protein or the 517 protein of *M. tuberculosis*. In this instance, the assayed sample such as sputum provides the antigen that is affixed to the solid phase matrix to form the solid support. An aqueous composition containing the anti-peptide antibodies or their idiotypic portions (binding site-containing portions) is admixed, maintained and separated from the solid phase as previously discussed for the presence of anti-65KD protein antibodies. The presence of bound anti-peptide antibodies is thereafter assayed to determine the presence of the *M. tuberculosis* antigen in the sample, following the broad admixture, separation and analysis steps previously described. Whole antibodies and their idiotype-containing portions such as Fab and $F(ab')_2$ portions are collectively referred to as paratoic molecules.

In exemplary studies, antibodies (paratopic molecules) were raised in New Zealand white rabbits to both the amino-terminal and carboxy-terminal polypeptide sequences (Peptides 1 and 54 of Table 4, hereinafter) of the 540 protein. Varying dilutions of pure *M. tuberculosis* cultures were bound to the walls of microtiter plates to form a solid support and one or the other of the two aqueous anti-peptide antibody preparations was admixed with the solid support to form a solid/liquid phase admixture. After maintaining the solid/liquid phase admixture for a time period sufficient for the anti-peptide antibodies to bind to the mycobacterial antigens present, the phases were separated. The solid phase was rinsed to assure removal of unbound anti-peptide antibodies. The presence of anti-peptide antibodies bound to the solid support was thereafter determined by standard methods.

As a result of those studies, it was determined that the presence of a mycobacterial antigen could be detected at a concentration of about $10^5$ organisms per well. qputum samples from persons with active infections of *M. tuberculosis* typically contain about 105–106 organisms in the volume of a sample utilized in the study. Thus, anti-peptide antibodies raised to a peptide of this invention such as those raised to Peptides 1 and 54 can be utilized to detect mycobacterial antigens present at a level found in a clinical environment.

Antibodies were similarly raised to the immunologically active recombinant, fusion, 540 protein produced by pTB22, and a similar antibody binding study was carried out. The results were generally similar to those discussed above, except that this assay was somewhat more sensitive, presumably as a result of the polyclonal character of the induced antibodies.

In addition to the above assays for mycobacterial antigens, several additional immunoassays can be carried out using antibodies induced (a) by the previously-mentioned 540 protein, or more particularly (b) by an immunologically active portion thereof such as the fusion protein produced by pTB22, a fusion protein that contains a peptide sequence of Tables 2 or 4 fused to a portion or all of another molecule such as beta-galactosidase, or by a peptide of Tables 2 and 4. Such additional immunoassays are well known in the art and include, for example, double antibody, sandwich, assays, [la]nd competition assays as where a peptide or other antigen described herein competes for the antibodies with a mycobacterial antigen in the assayed sample.

In each of the immunoassays, a sample to be assayed for the presence of a mycobacterial 65KD cell wall protein-a antigen is admixed in an aqueous medium with paratopic molecules raised to the 540 protein, or more particularly to an immunologically active portion thereof. The resulting admixture is maintained for a time period sufficient for the paratopic molecules to immunoreact with mycobacterial antigens present in the admixed sample to form an immunoreactant. The presence, and usually the amount, of immunoreactant formed is determined.

The anti-peptide paratopic molecules can themselves contain a label. Preferably, however, a second label-containing reagent is utilized that reacts with the bound paratopic molecules such as whole anti-peptide antibodies. The peroxidase-conjugated goat-anti-mouse antibodies utilized herein are exemplary of such reagents.

A solid phase assay kit that utilizes the anti-peptide antibodies or other paratopic molecules induced by an immunologically active portion of the 540 protein is also contemplated herein for clinical use of the before-described method. Here, the kit contains at least a solid phase matrix to which the assayed-for antigen of the sample or antibodies can be affixed in one package and a preparation of anti-peptide or anti-immunologically active 540 protein portion paratopic molecules that immunoreact with the 540 (65KD) protein or the 517 protein in a second package. Additional packages of reagents similar in type and function to those previously mentioned can also be included.

For inducing paratopic molecules such as whole antibodies, a useful peptide is typically linked to an antigenic carrier molecule such as keyhole limpet hemocyanin (KLH) as a conjugate, the conjugate is thereafter dispersed in a physiologically tolerable diluent as an inoculum, and the inoculum is injected into the laboratory mammal using well known procedures. The inoculated animal is maintained and given booster injections as required, until a desired antibody titer to the inducing peptide is achieved. The mammal's antibody-containing serum is thereafter obtained, purified as desired, and utilized in a diagnostic assay such as an SDS-PAGE/Western blot for the presence of a substantially corresponding protein.

The word "inoculum" in its various grammatical forms is used herein to describe a composition containing an amount of peptide conjugate, peptide polymer (as described hereinafter), 65KD protein or recombinant protein sufficient for a described purpose that is dissolved or dispersed in an aqueous, physiologically tolerable diluent. Exemplary diluents are well known and include water, physiological saline, phosphate-buffered saline, Ringer's solution, incomplete Freund's adjuvant and the like.

Inocula can contain varying amounts of a preferred peptide or polymer, depending upon its use.

Where paratopic molecules are to be formed or an inoculum is otherwise to be used as a vaccine, about 100–500 micrograms of peptide or peptide polymer are used per injection into laboratory animals such as mice, rabbits or guinea pigs. Larger amounts are utilized for larger mammals, as is known. Similar amounts of peptide or polymer are utilized for in vivo DCH assays.

Smaller amounts of antigenic peptide or antigenic peptide polymer are utilized for in vitro stimulation assays. Using 200 microliters (ul) of total volume and about $1-2\times10^4$ PBMC and about $1\times10^5$ antigen-presenting cells, concentrations of about 0.1 to about 50 micrograms of antigen per milliliter are useful.

Exemplary procedures for the chemical synthesis of a useful peptide as well as preparation of a conjugate and use of the conjugate to raise antibodies can be found in U.S. Pat. Nos. 4,636,463, 4,599,231, 4,599,230, 4,545,931, 4,544, 500, all of whose disclosures are incorporated herein by reference.

Another use for a preferred peptide of this invention is in an assay for the presence of mycobacterially-exposed (or immune); i.e., previously immunologically exposed, mononuclear cells such as T cells in a body sample containing such cells. Mycobacterially-exposed (or immune) mononuclear cells are cells that themselves have been immunologically exposed to a mycobacteri al immunogen or whose progenitor cells had been so exposed to such an immunogen. Thus, a preferred peptide can be used to determine whether a mammal has been immunized against a mycobacterium or has or has had a mycobacterial infection.

In such an assay, peripheral blood mononuclear cells, and particularly T cells, from the mammal are provided. Those cells are admixed and contacted in an aqueous cell culture medium with a stimulating amount of both antigen presenting cells and a preferred peptide of the invention to form a stimulatory cell culture. The stimulatory cell culture is maintained for a period of time sufficient for immune mononuclear cells present to be stimulated and to evidence that stimulation, usually about 18–96 hours and most usually 24–48 hours, under usual cell culture conditions. The presence of mononuclear cell stimulation is thereafter determined.

Where mononuclear cell stimulation is found, it indicates the presence in the assayed mononuclear cell population of cells which themselves were immunologically exposed to a mycobacterium or whose parental line was immunologically exposed to a mycobacterium.

As is illustrated by the results shown in Table 3, hereinbefore, the recombinant 540 protein and recombinant fusion protein containing a portion of the beta-galactosidase molecule and an immunologically active portion of the 540 protein were useful in stimulating mycobacteriologically-immune mononuclear cells in vivo in a DCH assay. Such molecules can be utilized in the above-described assay, and in the stimulatory assays described hereinafter in the same manner as can the peptides, and in the place of a peptide.

Mononuclear cell stimulation can be determined in a number of manners that are well known in the art, some of which are described specifically hereinafter. The cells of the mononuclear cell population that most usually are stimulated are T cells, and for that reason, the mononuclear cells will be usually referred to hereinafter as T cells. More particularly, T cells that exhibit the CD4 or T4 ($CD4^+$ or $T4^+$) antigen and those that exhibit the CD8 or T8 ($CD8^+$ or $T8^+$) antigen are the cells that are typically stimulated. Those T cells are often more generally referred to as helper and killer or cytotoxic T cells, respectively.

Exemplary manners in which T cell stimulation can be determined include (a) proliferation as assayed by the uptake of a radiolabeled nucleoside such as $[^3H]$-deoxythymidine also referred to as $[^3H]$-Tdr, $[^3H]$-thymidine ($[^3H]$-T), (b) secretion of interferon-gamma, (c) secretion of interleukin-2 (IL-2), (d) secretion of granulocyte macrophage-colony stimulating factor (GM-CSF), (e) cytotoxicity, a phenomenon that can occur with T cells such as $T4^+$ T cells as well as with $T8^+$ cells, (f) the ability to provide an in vitro B cell helper function, (g) the ability of immune T cell clones to provide a delayed cutaneous hypersensitivity (DCH) response in vivo as described herein and in U.S. Pat. No. 4,689,397 whose disclosures are incorporated by reference, and (h) the ability of immune T cell clones to provide protective immunity in vivo.

A kit is also contemplated for use with the immediately preceding assay. That kit can include a number of containers, at least one which contains a preferred peptide antigen of this invention or a polymer of such a peptide antigen whose repeating units are comprised of a "di-Cys-terminated" peptide as is described hereinafter. A mixture of two or more such preferred peptides or their polymers can also be present. A sufficient amount of a preferred peptide or peptide polymer is contained in the container to perform at least one assay using that method.

The assay kit can further include a premeasured amount of buffer or other salt for the preparation of an inoculum of the peptide or polymer upon the addition of water or other suitable aqueous medium. The inoculum can also be provided in premixed aqueous form either at the concentration for use or as an aqueous concentrate to be diluted.

Of course, the particular constituents and concentrations of those constituents can differ between in vitro and in vivo assays as well as between different mammals whose cells are to be assayed. Such constituents and concentrations can be readily determined by skilled workers. It is to be further understood that a previously described fusion protein that includes an immunologically active portion of a mycobacterial 65KD cell wall protein-a antigen can also be used to the exclusion of a peptide or polymer thereof as the antigen. Thus, the antigen of the kit can more broadly be described as a mycobacterial antigen.

A useful peptide corresponds substantially in sequence to a sequence of either the 540 or the 517 proteins discussed previously. Substantial correspondence of peptide sequences can be determined in a number of ways.

Of course, two peptides having identical sequences correspond substantially, as do to peptides that share identical sequences but also contain one or more further sequences. Similarly, two sequences that differ by conservative substitutions such as isoleucine for leucine or valine, asparatic acid for glutamic acid, asparagine for glutamine, arginine for lysine, serine for threonine, phenylalanine for tryptophan and tyrosine for phenylalanine, also correspond substantially.

Two sequences can also correspond substantially when antibodies raised to one immunoreact with another. For example, the particular peptides disclosed hereinafter can be used to raise antibodies that immunoreact with the 65KD (540) protein, and consequently, those peptides correspond substantially in sequence to the sequence of the 65KD protein.

Biochemical evidence from immunoassay and from analogy with conserved protein-protein interaction in solved X-ray crystallographic structures with differing sequences such as in the dimer contacts of oligomeric enzymes indicates that the conservation of protein-protein recognition does not require a strict conservation of sequence, for relatedness. Whereas single amino acid residue changes may affect such recognition to a wide degree depending upon the nature of the substitution, in general terms the relatedness and thus substantial correspondence of two differing amino acid sequences with respect to protein-protein (and antigenic and/or immunogenic) recognition can be expressed in terms of seven basic amino acid residue parameters:

(1) hydrophobicity;

(2) evolutionary occurrence of changes in known sequences;

(3) size of side chain;

(4) charge and polarity;

(5) preference for turned secondary structure;

(6) preference for beta strand secondary structure; and (7) preference for helical secondary structure.

To define the degree of sequence identity relevant to antigenic and/or immunogenic recognition, and thus substantial correspondence of peptide variants, a consensus matrix based upon the above seven criteria can also be used to assign numerical values for each amino acid residue pair in the sequences being considered for substantial correspondence. For the purposes of the present invention, a consensus matrix developed by Dr. Elizabeth Getzoff and Dr. John Tainer of the Scripps Clinic and Research Foundation of La Jolla, Calif. can be used. That consensus matrix is as follows, wherein the individual amino acid residues are designated by a one-letter code in the interests of conciseness:

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 7 | -5 | -1 | -2 | 0 | 0 | -1 | 2 | -1 | 0 | 1 | -2 | 2 | -1 | 0 | 0 | 0 | -3 | -3 | 1 |
| R | -5 | 10 | 0 | -1 | -3 | 2 | -1 | -5 | 5 | -4 | -4 | 5 | -3 | -2 | -3 | 0 | 0 | -1 | -1 | 4 |
| N | -1 | 0 | 6 | 3 | 1 | 3 | 0 | 1 | 3 | -2 | -2 | 2 | -1 | -3 | 1 | 4 | 2 | -3 | 0 | -2 |
| D | -2 | -1 | 3 | 7 | -2 | 1 | 4 | 0 | 0 | -3 | -3 | 0 | -2 | -4 | 0 | 1 | 0 | -5 | -2 | -3 |
| C | 0 | -3 | 1 | -2 | 7 | 1 | -2 | 1 | 0 | 0 | 0 | -2 | 0 | 0 | 0 | 3 | 4 | -2 | 2 | 0 |
| Q | 0 | 2 | 3 | 1 | 1 | 6 | 2 | -1 | 4 | 0 | 0 | 2 | 0 | 0 | 0 | 1 | 3 | -1 | 0 | 0 |
| E | -1 | -1 | 0 | 4 | -2 | 2 | 7 | -3 | 1 | -3 | -2 | 0 | -1 | -3 | -2 | 0 | 0 | -5 | -3 | -3 |
| G | 2 | -5 | 1 | 0 | 1 | -1 | -3 | 8 | -2 | -3 | -3 | -2 | -2 | -5 | 2 | 3 | 1 | -6 | -2 | -2 |
| H | -1 | 5 | 3 | 0 | 0 | 4 | 1 | -2 | 8 | -1 | 0 | 4 | 0 | 0 | 0 | 1 | 2 | 0 | 2 | -1 |
| I | 0 | -4 | -2 | -3 | 0 | 0 | -3 | -3 | -1 | 5 | 4 | -3 | 2 | 2 | -2 | -2 | 0 | 0 | 0 | 4 |
| L | 1 | -4 | -2 | -3 | 0 | 0 | -2 | -3 | 0 | 4 | 6 | -2 | 4 | 3 | -1 | -2 | 0 | 1 | 0 | 3 |
| K | -2 | 5 | 2 | 0 | -2 | 2 | 0 | -2 | 4 | -3 | -2 | 8 | -1 | -3 | -1 | 0 | 0 | -4 | -2 | -3 |
| M | 2 | -3 | -1 | -2 | 0 | 0 | -1 | -2 | 0 | 2 | 4 | -1 | 6 | 2 | 0 | -1 | 0 | 0 | -1 | 2 |
| F | -1 | -2 | -3 | -4 | 0 | 0 | -3 | -5 | 0 | 2 | 3 | -3 | 2 | 7 | -2 | -3 | 0 | 4 | 3 | 2 |
| P | 0 | -3 | 1 | 0 | 0 | 0 | -2 | 2 | 0 | -2 | -1 | -1 | 0 | -2 | 7 | 2 | 1 | -4 | -1 | -1 |
| S | 0 | 0 | 4 | 1 | 3 | 1 | 0 | 3 | 1 | -2 | -2 | 0 | -1 | -3 | 2 | 5 | 3 | -3 | 0 | -1 |
| T | 0 | 0 | 2 | 0 | 4 | 3 | 0 | 1 | 2 | 0 | 0 | 0 | 0 | 0 | 1 | 3 | 6 | -2 | 1 | 0 |
| W | -3 | -1 | -3 | -5 | -2 | -1 | -5 | -6 | 0 | 0 | 1 | -4 | 0 | 4 | -4 | -3 | -2 | 9 | 2 | 0 |
| Y | -3 | -1 | 0 | -2 | 2 | 0 | -3 | -2 | 2 | 0 | 0 | -2 | -1 | 3 | -1 | 0 | 1 | 2 | 8 | 0 |
| V | 1 | -4 | -2 | -3 | 0 | 0 | -3 | -2 | -1 | 4 | 3 | -3 | 2 | 2 | -1 | -1 | 0 | 0 | 0 | 5 |

Sequence comparison using the foregoing consensus matrix involves the determination of all possible alignments and the subsequent scoring of these alignments by the matrix. Two sequences are then aligned by computing the maximum match score from the consensus matrix. An alignment score in standard deviation units can be determined by taking the difference between the maximum matched score and the average maximum matched score for random permutation of the two sequences, and then dividing by the standard deviation of the random score.

For the present purposes, a consensus matrix score greater than three standard deviations (approximately an average value of about 3 per residue) shows significant relatedness at a confidence level of more than 99.7%. This is a restrictive criterion since it gives a frequency of 0.005 for all 5-residue peptides and 0.0014 for all 13-residue peptides occurring in 2222 known protein sequences. Similarly, a consensus matrix score greater than two standard deviations (approximately an average value of about 2 per residue) shows substantial correspondence to be significant at a confidence level of more than 95.4%.

To determine substantial correspondence for the purposes of the present invention, the consensus matrix score is calculated by ascertaining the matrix value for each aligned amino acid residue pair under consideration, and then summing the individual values for each such pair. The obtained sum is then compared against the number of standard deviations signifying the desired confidence level. If the obtained sum is greater than the product of the selected number of standard deviations times the number of amino acid residue pairs under consideration, then the amino acid residue sequences being compared correspond substantially to the indicated confidence level.

For example, to ascertain the substantial correspondence of the amino acid residue sequences —Lys—Trp—Phe—Cys—Gly— and

—Arg—Ile—Phe—Cys—Gly— the consensus matrix yields the following values

| | Value |
|---|---|
| —Lys— & —Arg— or K & R | 5 |
| —Trp— & —Ile— or W & I | 0 |
| —Phe— & —Phe— or F & F | 7 |
| —Cys— & —Cys— or C & C | 7 |
| —Gly— & —Gly— or G & G | 8 |
| Total | 27 |

For substantial correspondence at the 99.7% confidence level, the consensus matrix score must exceed the number of amino acid residue pairs under consideration times 3; i.e., 5×3 or 15. Inasmuch as 27 is greater than 15, substantial correspondence is indeed present for the above two peptide sequences.

For the purposes of the present invention, substantial correspondence among peptides within the scope of the invention preferably is present at least to about 95% confidence level, and more preferably to at least about 99% confidence level.

A DNA sequence can correspond substantially to another DNA sequence if both sequences contain sequences of fifteen bases that are in phase and identical, or bases that are not identical but code for an identical sequence of amino acid residues, or code for amino acid residue sequences that correspond substantially. Thus, amino acid residue sequences that correspond substantially are encoded by DNA sequences that correspond substantially.

It is to be noted that two or more peptide sequences can substantially correspond as determined by one or both of the latter two definitions and still exhibit different immunoreactivities with antibodies raised to the intact protein as is found in nature or with T cells stimulated by such natural proteins. An example of this phenomenon is discussed hereinafter.

In addition to the specific peptides disclosed in Table 2, hereinbefore, further peptides that correspond in sequence to a portion of the 540 protein sequence are also useful herein. A list of those peptides is provided in Table 4, below.

TABLE 4

Peptides

| Peptide Number | Residues[1] | Sequence[2] | | | | | | | | | | | | | | |
|---|---|---|---|---|---|---|---|---|---|---|---|---|---|---|---|---|
| 1 | 1–15 | M | A | K | T | I | A | Y | D | E | E | A | R | R | G | L |
| 2 | 11–25 | A | R | R | G | L | E | R | G | L | N | A | L | A | D | A |
| 3 | 21–35 | A | L | A | D | A | V | K | V | T | L | G | P | K | G | R |
| 4 | 31–45 | G | P | K | G | R | N | V | V | L | E | K | K | W | G | A |
| 5 | 41–55 | K | K | W | G | A | P | T | I | T | N | D | G | V | S | I |
| 6 | 51–65 | D | G | V | S | I | A | K | E | I | E | L | E | D | P | Y |
| 7 | 61–75 | L | E | D | P | Y | E | K | I | G | A | E | L | V | K | E |
| 8 | 71–85 | E | L | V | K | E | V | A | K | K | T | D | D | V | A | G |
| 9 | 81–95 | D | D | V | A | G | D | G | T | T | T | A | T | V | L | A |
| 10 | 91–105 | A | T | V | L | A | Q | A | L | V | R | E | G | L | R | N |
| 11 | 101–115 | E | G | L | R | N | V | A | A | G | A | N | P | L | G | L |
| 12 | 111–125 | N | P | L | G | L | K | R | G | I | E | K | A | V | E | K |
| 13 | 121–135 | K | A | V | E | K | V | T | E | T | L | L | K | G | A | K |
| 14 | 131–145 | L | K | G | A | K | E | V | E | T | K | E | Q | I | A | A |
| 15 | 141–155 | E | Q | I | A | A | T | A | A | I | S | A | G | D | Q | S |
| 16 | 151–165 | A | G | D | Q | S | I | G | D | L | I | A | E | A | M | D |
| 17 | 161–175 | A | E | A | M | D | K | V | G | N | E | G | V | I | T | V |
| 18 | 171–185 | G | V | I | T | V | E | E | S | N | T | F | G | L | Q | L |
| 19 | 181–195 | F | G | L | Q | L | E | L | T | E | G | M | R | F | D | K |
| 20 | 191–205 | M | R | F | D | K | G | Y | I | S | G | Y | F | V | T | D |
| 21 | 201–215 | Y | F | V | T | D | P | E | R | Q | E | A | V | L | E | D |
| 22 | 211–225 | A | V | L | E | D | P | Y | I | L | L | V | S | S | K | V |
| 23 | 219–233 | L | L | V | S | S | K | V | S | T | V | K | D | L | L | P |
| 24 | 231–245 | L | L | P | L | L | E | K | V | I | G | A | G | K | P | L |
| 25 | 241–255 | A | G | K | P | L | L | I | I | A | E | D | V | E | G | E |
| 26 | 251–265 | D | V | E | G | E | A | L | S | T | L | V | V | N | K | I |
| 27 | 261–275 | V | V | N | K | I | R | G | T | F | K | S | V | A | V | K |
| 28 | 271–285 | S | V | A | V | K | A | P | G | F | G | D | R | R | K | A |
| 29 | 281–295 | D | R | R | K | A | M | L | Q | D | M | A | I | L | T | G |
| 30 | 291–305 | A | I | L | T | G | G | Q | V | I | S | E | E | V | G | L |
| 31 | 301–315 | E | E | V | G | L | T | L | E | N | A | D | L | S | L | L |
| 32 | 311–325 | D | L | S | L | L | G | K | A | R | K | V | V | V | T | K |
| 33 | 321–335 | V | V | V | T | K | D | E | T | T | I | V | E | G | A | G |
| 34 | 331–345 | V | E | G | A | G | D | T | D | A | I | A | G | R | V | A |
| 35 | 341–355 | A | G | R | V | A | Q | I | R | Q | E | I | E | N | S | D |
| 36 | 351–365 | I | E | N | S | D | S | D | Y | D | R | E | K | L | Q | E |
| 37 | 361–375 | E | K | L | Q | E | R | L | -A | K | L | A | G | G | V | A |
| 38 | 371–385 | A | G | G | V | A | V | I | K | A | G | A | A | T | E | V |
| 39 | 381–395 | A | A | T | E | V | E | L | K | E | R | K | H | R | I | E |
| 40 | 391–405 | K | H | R | I | E | D | A | V | R | N | A | K | A | A | V |
| 41 | 401–415 | A | K | A | A | V | E | E | G | I | V | A | G | G | G | V |
| 42 | 411–425 | A | G | G | G | V | T | L | L | Q | A | A | P | T | L | D |
| 43 | 421–435 | A | P | T | L | D | E | L | K | L | E | G | D | E | A | T |
| 44 | 431–445 | G | D | E | A | T | G | A | N | I | V | K | V | A | L | E |
| 45 | 441–455 | K | V | A | L | E | A | P | L | K | Q | I | A | F | N | S |
| 46 | 451–465 | I | A | F | N | S | G | L | E | P | G | V | V | A | E | K |
| 47 | 461–475 | V | V | A | E | K | V | R | N | L | P | A | G | H | G | L |
| 48 | 471–485 | A | G | H | G | L | N | A | Q | T | G | V | Y | E | D | L |
| 49 | 481–495 | V | Y | E | D | L | L | A | A | G | V | A | D | P | V | K |
| 50 | 491–505 | A | D | P | V | K | V | T | R | S | A | L | Q | N | A | A |
| 51 | 501–515 | L | Q | N | A | A | S | I | A | G | L | F | L | T | T | E |
| 52 | 511–525 | F | L | T | T | E | A | V | V | A | D | K | P | E | K | E |
| 53 | 521–535 | K | P | E | K | E | K | A | S | V | P | G | G | G | D | M |
| 54 | 526–540 | K | A | S | V | P | G | G | G | D | M | G | G | M | D | F |

[1],[2]See Notes 1 and 2 of Table 2.

Preferred peptides for use in the previously described assay for the presence of mycobacteriallyimmune mononuclear cells are those that are numbered as follows, wherein the numbers are those shown in one or both of Tables 2 and 4, and whose sequence positions in the 540 protein are given in parentheses: Peptide 22 (211–225); Peptide 23 (219–233); Peptide 24 (231–245); Peptide 30 (291–305); Peptide 46 (451–465); Peptide 58 (11–28); Peptide 59 (66–79); Peptide 60 (114–130); and Peptide (394–408).

Several proliferative assays were conducted using the peptides of the invention. Results of those studied are shown and discussed below.

One study was carried out using pooled peripheral blood mononuclear cells (PBMC) from *M. bovis* BCG-vaccinated humans. The details of this study are described in the Materials and Methods Section. Briefly, PBMC were isolated and seeded into culture plate wells. Such PBMC populations contain their own endogenous antigen-presenting or feeder cells. A peptide of the invention was added as antigen at either 0.1 microgram per milliliter (ug/ml), 1 ug/ml or 10 ug/ml of culture. The antigen/cell culture mixture was maintained for a time period of six days, at which time, radiolabeled thymidine was admixed. The cultures were harvested eighteen hours later and the thymidine incorporation was measured in a liquid scintillation counter. The results of this study are shown in Table 5, below.

TABLE 5

Protein 540
Peptide-Induced PBMC Proliferation[1]

| Peptide Number[2] | Residue Positions[3] | Proliferation Response[4] |
|---|---|---|
| 10 | 91–105 | – |
| 21 | 201–215 | – |
| 22 | 211–225 | ++ |
| 24 | 231–245 | ++ |
| 25 | 241–255 | – |
| 30 | 291–305 | ++ |
| 35 | 341–355 | – |
| 43 | 421–435 | – |
| 46 | 451–465 | +++ |
| 47 | 461–475 | – |
| 48 | 471–485 | – |
| 49 | 481–495 | – |
| 53 | 521–535 | – |
| 54 | 526–540 | – |
| 58* | 11–28 | ++ |
| 59* | 66–79 | ++ |
| 60* | 114–130 | +++ |
| 61* | 154–172 | – |
| 23* | 219–233 | +++ |
| 62* | 394–408 | +++ |
| 63* | 494–508 | – |

[1]Proliferation as measured by incorporation of [$^3$H]-thymidine in counts per minute (cpm).
[2]Peptide number as shown in Tables 2 and 4.
[3]Peptide residue sequence positions as shown in Tables 2 and 4 and in FIG. 2.
[4]Proliferative response reported at the optimal peptide concentration is represented as follows: "+++" = 10,000–40,000 cpm; "++" 2000–10,000 cpm; or "–" = 300–700 cpm. Proliferation in the absence of peptide antigen was 421 ± 37 cpm, and was 82,857 ± 2,913 cpm in the presence of an extract of *M. tuberculosis*. Standard deviations did not exceed 15 percent in any of the triplicate measurements.
* Peptides predicted to form amphiphilic helices.

The above results indicate that nine of the twenty petides assayed elicited a strong proliferative response. Thus, nine regions of the 540 protein were identified as human T cell antigens.

Seven regions of the 540 protein were predicted by computer-assisted analysis to form amphiphilic helices. Regions that can form amphiphilic helices appear to have a higher probability of being recognized by T cells. Berzofsky, (1985) *Science*, 229:932–940. However, only five of those seven peptides provided a proliferative response. This indicates that amphiphilicity is neither sufficient nor necessary for a peptide to interact with T cells.

In further studies with PBMC from individual BCG-immunized humans, an influence of HLA type was noted on reactivity. Thus, ! ymphocytes from two persons with the HLA-DR4 allele reacted with Peptide 62 (positions 364–408) but not with Peptide 30 (positions 291–305), whereas cells from three persons with the HLA-DR1 allele reacted with Peptide 30 but not with Peptide 62.

The above results indicate a genetic, HLA restriction on the prolieration response. Thus, a mixture of preferred peptides or their polymers is preferred when assaying an out bred population such as humans so that false negative responses can be minimized.

Another proliferation study was carried out with sixteen of the above peptides. The proliferating cells here were either one of two T cell clones or a polyclonal T cell line. One T cell clone came from a tuberculosis patient (AH) and is designated K8AH. The second T cell clone was obtained from a person (JM) vaccinated with heat-killed *M. leprae* and is referred to as A7JM. The polyclonal T cell line (JM) was also obtained from the cells of JM that were initially stimulated with *M. bovis* BCG, stored frozen and thereafter stimulated with a recombinant 65KD protein from *M. tuberculosis* (Oftung et al., (1987) *J. Immunol.*, 138:927–931].

Proliferation was again assayed by the [$^3$H]-thymidine incorporation method. Here, autologous PBMC irradiated to inhibit proliferation but sufficiently viable to act as antigen-presenting cells were added to the cultures of both isolated T cell clones and the cell line along with a mycobacterial antigen. After three days of maintenance, the cultures were pulsed with the radiolabel for four hours, harvested and then counted.

The details of this study are provided in the Materials and Methods Section. The results are shown in Table 6, below.

TABLE 6

Protein 540
Peptide-Induced Proliferation[1]

| Peptide[2] Number | Proliferative Response[3] | | |
|---|---|---|---|
| | K8AH | A7JM | JM |
| 59* | 0.3 ± 0.1 | 0.2 ± 0.1 | 0.3 ± 0.2 |
| 10 | 0.4 ± 0.2 | 0.1 ± 0 | 0.2 ± 0 |
| 21 | 0.3 ± 0 | 0.1 ± 0 | 0.2 ± 1 |
| 22 | 0.5 ± 0 | <u>14.0±2.0</u> | <u>88.2±15.8</u> |
| 23* | 0.2 ± 0.1 | 0.1 ± 0.1 | <u>9.0±2.8</u> |
| 24 | <u>7.4±0.3</u> | 0.1 ± 0 | <u>4.1±0.1</u> |
| 25 | 0.9 ± 0.2 | 0.1 ± 0 | 0.3 ± 0.2 |
| 30 | 0.4 ± 0.1 | 0.1 ± 0 | 0.7 ± 0.2 |
| 35 | 0.4 ± 0.1 | 0.4 ± 0 | 0.3 ± 0.1 |
| 62* | 0.4 ± 0.3 | 0.2 ± 0 | 0.3 ± 0.1 |
| 43 | 0.3 ± 0.1 | 0.1 ± 0.1 | 0.2 ± 0.1 |
| 46 | 0.5 ± 0.1 | 0.5 ± 0 | <u>11.4±0.2</u> |
| 49 | 0.5 ± 0.1 | 0 ± 0 | 0.4 ± 0.3 |
| 53 | 0.1 ± 0 | 0.2 ± 0.1 | 0.2 ± 0.1 |
| 54 | 0.4 ± 0.2 | 0.2 ± 0.1 | 0.9 ± 0.1 |
| 63 | 0.4 ± 0 | 0.2 –0.1 | 0.4 ± 0.1 |
| –Ag[4] | 0.5 ± 0.2 | 0.3 ± 0.2 | 0.4 ± 0.2 |
| *M. tuberculosis* rec. 65 KD[5] | <u>4.3±0.5</u> | <u>12.3±1.9</u> | <u>30.1±2.6</u> |
| *M. tuberculosis*[5] | <u>8.5±1.6</u> | <u>11.5±1.5</u> | <u>118.7±5.4</u> |
| *M. bovis* BCG[5] | <u>9.4±0.7</u> | <u>21.6±2.3</u> | <u>183.4±19.0</u> |
| *M. leprae*[5] | <u>0.5±0.1</u> | <u>24.2±2.0</u> | <u>119.7±15.5</u> |

[1,2]See notes of Table 5.
[3]Proliferative responses, in cpm × $10^{-3}$ ± standard derviation for two or three replicate studies using 10 ug/ml of each peptide. Positive values are underlined.
[4]Response in the absence of antigen.
[5]Affinity-purified recombinant *M. tuberculosis* 65 KD protein at 50 ug/ml and whole mycobacteria at 20 ug/ml.

The results shown in Table 6 illustrate the clonal specificity for antigens of the screened peptides. Thus, T cell clone K8AH, specific to the *M. tuberculosis* complex [Oftung et al., (1987) *J. Immunol.*, 138:927–931] exhibited a proliferative response upon stimulation with an inoculum containing Peptide 24 (231–245). The T cell clone A7JM, which shows cross-reactivity to *M. tuberculosis* and *M. leprae*, responded to stimulation by admixture and contact with an inoculum containing a different segment of the 65KD (540 protein) represented by Peptide 22 (211–225), but not to inocula containing the flanking and overlapping Peptides 21 (201–215) and 23 (219–233).

The JM polyclonal T cell line also proliferated in response to contacting with inocula containing Peptides 24 and 22. That cell line also showed a significant proliferation in response to admixture and contact with an inoculum containing Peptide 23, whose sequence overlaps both of those sequences of Peptides 24 and 22, and that was predicted to form an amphiphilic helix. Contacting the polyclonal T cell line with an inoculum containing Peptide 46 (positions 451–465) also provided significant stimulation.

The genomic sequence of the 65KD protein of *M. leprae* and the putative translation product of that gene have been published. [Mehra et al., (1986) *Proc. Natl. Acad. Sci. USA*, 83:7013–7017.] A comparison of the 65KD protein amino acid residue sequences from *M. leprae* and *M. tuberculosis* shows the two sequences to be very similar, with only a relatively few different residues between them.

T cell clone A7JM had previously been shown to proliferate in response to stimulation by both whole *M. leprae* and whole *M. tuberculosis*. [Mustafa et al., (1986) *Lepr. Rev. Suppl.*, 2:123–130.] Consistent with those findings, clone A7JM also proliferated when admixed and contacted with an inoculum containing Peptide 64, below, whose sequence differed from that of Peptide 22 by the conservative change of the residue at position 215 from glutamic acid of Peptide 22 to aspartic acid.

Further stimulation studies were carried out using *M. leprae*-related and *M. tuberculosis* pepides and the beforementioned T cell clones and cell line. An inoculum containing Peptide 23 caused stimulation of the polyclonal cell line. The sequence of that peptide is identical in both *M. leprae* and *M. tuberculosis*. (See also Table 6.)

In addition, two *M. leprae*-related Peptides, 64 and 66, that each contain a single amino acid residue substitution as compared to their analogous *M. tuberculosis*-related Peptides, 22 and 46, respectively, also were capable of eliciting stimulation of *M. leprae*-immune cell line JM when inocula containing one or the other were admixed and contacted with those cells. Neither *M. leprae*-related Peptide 64 nor Peptide 66 stimulated cells of T cell clone K8AH. The sequences of Peptide 66 and of its analogous Peptide 46 are shown below.

| (22) | A | V | L | E | D | P | Y | I | L | L | V | S | S | K | V  |
| (64) | A | V | L | E | E | P | Y | I | L | L | V | S | S | K | V. |

T cell clone K8AH is able to discriminate between *M. tuberculois* and *M. leprae* presented for stimulation as whole bacilli, and was similarly able to exhibit the same discrimination at the peptide level. Thus, the *M. tuberculosis*-related Peptide 24 (231–245) could be used to stimulate clone K8AH, whereas contact with an inoculum containing Peptide 65, below, having the analogous *M. leprae* sequence did not stimulate that clone to proliferate. Inocula containing Peptide 65 also did not stimulate clone A7JM or polyclonal cell line JM.

| (24) | L | L | P | L | L | E | K | V | I | G | A | G | K | P | L  |
| (65) | L | L | P | L | L | E | K | V | I | Q | A | G | K | S | L. |

As can be seen from a comparison of the above sequences of Peptides 24 and 65, those peptides differ by the substitution of two residues near their carboxy-termini. The glycine (G) at position 240 of Peptide 24 is substituted as a glutamine (Q) in Peptide 65, and the proline (P) at position 244 of Peptide 24 is substituted as a serine (S) in Peptide 65.

| (46) | I | A | F | N | S | G | L | E | P | G | V | V | A | E | K  |
| (66) | I | A | F | N | S | G | M | E | P | G | V | V | A | E | K. |

Thus, recognition of Peptide 24 by clone K8AJ must be influenced by one or both of glycine-240 and proline-244. Interestingly, an inoculum containing Peptide 25 (241–255), which contains proline-244, did not cause stimulation of clone K8AH cells when admixed and contacted with those cells.

A blocking study was carried out to determine whether an inoculum containing Peptide 65 could inhibit the stimulatory response caused by Peptide 24 on cells of T cell clone K8AH. Those studies showed that the *M. leprae*-related Peptide 65 could not block the response induced by the *M. tuberculosis*-related Peptide 24. This finding again implies the criticality of one or both of the residues at positions 240 and 244 of Peptide 24.

Each of Peptides 64, 65 and 66 corresponds substantially to Peptide 22, 24 and 46, respectively. That substantial correspondence notwithstanding, the results above illustrate that there can be differences in reactivities of such peptides at the T cell level.

That different reactivities in T cell stimulation were found for substantially corresponding peptides that differed in sequence is not particularly surprising in view of the type of interaction thought to be involved in T cell stimulation by an antigen as compared to an antigen-antibody interaction.

Thus, an antigen-antibody interaction is usually considered to be a relatively simple ligand-receptor interaction in which substitutions of polar for polar (e.g., glutamic for aspartic in Peptides 22 and 66) or apolar for apolar of about the same size (e.g., leucine for methionine in Peptides 46 and 67) typically are not of great consequence. Indeed, it has been shown that for some influenza-related 13-residue peptides, drastic substitutions can occur with little differences being noted in binding by a monoclonal antibody raised to the parent peptide. See, for example U.S Pat. No. 4,631,211.

T cell stimulation, on the otherhand, is thought to resemble a sandwich in which the T cell and the antigen-presenting or feeder cell are the bread and the antigen is the filling. Thus, a peptide antigen must bind to two receptors, one on the T cell, and the other, believed to be one or more proteins of the major histocompatibility complex (MCH), on the feeder cell. In addition, the binding between anti gen and each of the T cell and feeder cell receptors is thought to be weaker than is the usual antigen-antibody binding. It was not therefore surprising that the glycine to glutamine and proline to serine substitutions between Peptides 24 and 65 resulted in differences in T cell stimulation.

As noted previously, T cell stimulation can be manifest in a number of manners. The previous discussion has centered primarily on in vitro and in vivo proliferation assays. The results discussed below using T cell clones K8AH and A7JM illustrate further manisfestations of T cell stimulation, and manners in which such stimulation can be determined.

Standard assays for secretion of IL-2, granulocyte macrophage-colony stimulating factor (GM-CSF) and interferon-gamma secretion into the supernatants of aqueous stimulatory T cell cultures were conducted using the above cloned T cells to illustrate stimulation. Cytotoxicity against macrophages pulsed with the same stimulatory peptide or whole mycobacteria was also assayed. Details of these studies are provided in the Materials and Methods Section. The results are shown in Table 7, below.

TABLE 7

Protein 540 Peptide–Induced Stimulatory Responses In T Cell Clones[1]

| T cell clones[2] | IL-2 | GM-CSF[4] | IFN-Gamma[5] | Cytotoxicity[6] |
|---|---|---|---|---|
| K8AH + APC | <0.2 | 11 ± 12 (9%) | 10 | ND[7] |
| K8AH + APC + Peptide 24 | 9.4 + 0.6 | 153 + 30 (>100%) | 56 | 86.5 ± 0.6 |
| K8AH + APC + M. tuberculosis | 7.6 ± 0.2 | 87 ± 35 (71%) | 44 | 85.8 ± 2.9 |
| A7JM + APC | 0.2 | 5 ± 8 (4%) | 5 ± 1 | ND |
| A7JM APC + Peptide 22 | 6.8 ± 0.6 | 135 ± 4 (>100%) | 63 ± 7 | 82.7 ± 10 |
| A7JM + APC + M. tuberculosis | 6.8 ± 0.1 | 160 ± 14 (>100%) | 40 | 84.7 ± 3 |

[1]T cell clones were stimulated by the peptide antigen shown hereinbefore to specifically activate each clone. Stimulation was assayed by four methods. T cells and antigen-presenting cells (APC) without antigen were used as negative controls in all assays. Results are expressed as the mean ± standard deviation (where calculated) of duplicate or triplicate cultures.
[2]Culture contents in addition to the medium are shown in each entry, with plus signs (+) indicating the presence of mixed cellular components and antigen (peptide or M. tuberculosis), where present.
[3]Results expressed in units per ml.
[4]Assay based on three independent studies using three different bone marrow donors. Results are expressed in colony-forming units of GM per 2 × 10⁵ cells. Parenthesized percentages relate to the number of colonies induced by a GM-CSF positive control supernatant.
[5]Results expressed international units per ml.

TABLE 7-continued

Protein 540 Peptide–Induced Stimulatory Responses In T Cell Clones[1]

| T cell clones[2] | IL-2 | GM-CSF[4] | IFN-Gamma[5] | Cytotoxicity[6] |
|---|---|---|---|---|

[6]Results expressed as percentages as discussed in the Materials and Methods Section. APC + antigen was used as a negative control.
[7]ND = not done.

The results of Table 7 illustrate further standard techniques that are useful in determining the presence of stimulated T cells in addition to the proliferation assays discussed before.

Assays of T cell clones K8AH and A7JM indicated that both showed the helper/inducer (T4$^+$, T8$^-$) phenotype. Cells of the T4$^+$ phenotype are primarily helper cells that recognize antigen plus class II HLA proteins. Such cells are also known to exhibit cytotoxicity as is shown in Table 7.

Tuberculosis is a disease in which the cellular portion of the immune response is involved to the substantial exclusion of the humoral (antibody) portion of the immune response. Thus, the ability of the preferred peptide antigens to stimulate the T cell clones to not only proliferate but to also secrete IL-2, GM-CSF, and interferon gamma, each of which constitutes a portion of the cellular immunity response, indicates that those peptides, their polymers, and mixtures thereof, as well as the 540 protein (65 KD protein) can play an important role in protective immunity.

That role in cellular immunity is underscored by the macrophage cytotoxicity exhibited by the clones stimulated by the peptides or the whole mycobacteria. Similar cytotoxicity for other mycobacteria-reactive T cell clones has been reported. [Mustafa et al., (1987), *Clin. Exp. Immunol.*, 69:255–262; Kaufman et al. (1986), *Lep. Rev.* 57, Suppl. 2:101–111.] However, it is believed that the above results are the first demonstration that the same sequence of one protein antigen are involved in both T cell help and cytotoxicity. The in vivo role of such T4$^+$ cytotoxic T cells is believed to destroy those macrophages that have become incompetent to kill their intracellularly-growing mycobacteria.

A preferred peptide was previously described herein as being capable of stimulting mycobacterially-immune mononuclear cells, and such a peptide was said to be useful in assaying for present or prior immunological exposure of such cells to mycobacteria. A particularly preferred peptide or its polymer is also capable of immunizing an animal for protection against mycobacterial infection such as *M. tuberculosis*.

Thus, the present invention also contemplates a vaccine against mycobacteria such as *M. tuberculosis* that comprises a physiologically tolerable diluent containing as immunogen an immunizing effective amount of (i) a peptide whose amino acid residue sequence corresponds substantially to a particularly preferred T cell-stimulating peptide described herein or (ii) a polymer of such a particularly preferred T cell stimulating peptide as described herein.

Exemplary particularly preferred peptides include Peptides 22 and 24. Further particularly preferred peptides are those whose sequences correspond substantially to a sequence of the *M. tuberculosis* 540 protein or another mycobacterial 65 KD protein and contain 5 to about 40, more preferably about 10 to about 20 residues, and still further are capable of stimulating proliferation of mycobacterially-immune, and for a tuberculosis vaccine, *M. tuberculosis*-immune, T cells that exhibit the T4$^+$ and/or T8$^+$ phenotype.

Further particularly preferred peptides can be obtained by following a procedure similar to that discussed previously. Polyclonal T cells from one or more individuals are contacted with an inoculum containing a peptide such as one of those of Tables 2 and 4, and more particularly peptides such as those of Tables 5 and 6 that have already been shown capable of stimulating proliferation of mycobacterially-immune T cells. The peptides inducing proliferation are noted and the proliferating T cells are cloned by the limiting dilution technique as described by Of tung et al., (1987) *J. Immunol.*, 138:927–931. The phenotypes of the proliferated T cells are determined as with the OKT series of monoclonal antibodies available from Ortho Diagnostic Systems, Inc. of Raritan, N.J. One or more of the peptides capable of causing proliferation of T cells having the $T4^+$ and/or $T8^+$ phenotype is utilized in the vaccine.

More preferably, a mixture of peptides, polymers having such peptides as repeating units, or a polymer whose repeating units are a mixture of such peptides that cause proliferation of $T4^+$ and/or $T8^+$ T cells is used. The reason of this preference stems from the already noted MHC restriction. In addition, there is usually found an MHC restriction between $T4^+$ and $T8^+$ T cells, the former recognizing antigen plus class II MHC protein and the latter recognizing antigen plus class I MHC protein.

Peptides that correspond substantially to portions of the 517 protein are also useful herein, and are defined as to substantial correspondence similarly to those peptides discussed before. The peptides substantially corresponding to a sequence of the 517 protein can contain as few as five residues and are therefore somewhat shorter than are the shortest of the peptides discussed before.

Three peptides (denominated 55, 56 and 57) and their variants substantially correspond to sequences, written from left to right in the direction from amino-terminus to carboxy-terminus and using one letter code, having the formulas

| | | | | | | | | | | | | | |
|---|---|---|---|---|---|---|---|---|---|---|---|---|---|
| 55) | N | N | N | I | G, | | | | | | | | |
| 56) | X | G | N | Z | G, | and | | | | | | | |
| 57) | F | N | S | G | S | G | N | I | G | F(I) | G | N | S | G | wherein X is an amino acid residue selected from the group consisting of F, S, T, L, D and T; Z is an amino acid residue selected from the group consisting of T, I, L, S and V; and the parenthesized residue can replace the residue shown to its left in the sequence. Thus, in peptide 57, F and I are alternative residues. More preferably, X is selected from the group consisting of F, S and T; and Z is selected from the group consisting of T and I.

Using the before-described consensus matrix to calculate whether the variant pentapeptides defined hereinbefore by the consensus sequence XGNZG correspond substantially, one finds that all of those variants correspond substantially at least at 99% confidence level. This can be readily seen by determining the greatest differences caused by substitutions, then calculating the resultant consensus matrix score, and comparing that value to 3 times the number of residues compared, 5, (3×15=15).

Thus, for the X residue, substituting an Ile (I) for an Asp (D) residue, or a Ser (S) for a Phe (F) provides a value of −3 from the matrix. Similarly for Z, substitution of Ile (I) for Ser (S) or Ser (S) for Val (V) provides a value of −2 from the matrix. Since two Gly (G) residues and the Asn (N) residues are present in any of the before compared consensus pentapeptide sequences, the presence of those residues provides a score of 22 (8+6+8=22). Subtraction of five

[(−3)+(−2)] for the above substitutions from 22 provides a total score for the compared pentapeptides of 17.

Since 17 is greater than 15, any of the above substitutions to the consensus sequence provides pentapeptides that correspond substantially at least at the 99% confidence level. Furthermore, since the above substitutions caused the greatest numerical difference in the total score, any other of the before-discussed substitutions for both X and Z in the consensus sequence produces a total score; i.e., where X is Thr or Leu and Z is Thr or Leu, in the consensus sequence produces a total score that is larger than 17, and consequently, all of those pentapeptides also correspond substantially to each other at least at the 99% confidence level.

Peptides 55 and 56 are typically utilized as one of a plurality of repeating units of a polymer having a relatively low molecular weight; i.e., less than about 10,000 daltons in weight. The smallest such polymer, or oligomer, contains two of the five residue peptides (pentapeptides) bonded together through a peptide bond formed between the carboxy-terminal residue of a first pentapeptide repeating unit and the amino-terminal residue of a second pentapeptide repeating unit.

For example, Peptide 57, above, can be viewed as a polymer or oligomer having two such pentapeptide repeating units bonded together by a peptide bond, and also containing an additional four residues at the amino-terminus of the oligomer.

Similar calculations can also be carried out for variants of the other peptides disclosed herein as one means of determining whether a peptide with a different sequence from one of those specifically enumerated corresponds substantially to a specifically enumerated peptide, or to a portion thereof. For the purposes of epitope-paratope interactions, sequences containing at least five residues are the shortest sequences that should be compared since at least five or six residues appear to be required for epitope-paratope interaction. See for example, Elder et al. (1987) *J. Virol.* 61:8–15; Atassi (1975) *Immunochemistry* 12:423–438; and Benjamini et al. (1969) *Biochemistry* 8:2242–2246.

Similarly, the sequence in isolated form

NNNIGNNNIGNNNIG that is also present at nucelotide positions 3270 through 3226 of FIG. 2 can be considered a polymeric or oligomeric trimer of the sequence of peptide 55. Likewise, an isolated form of the sequence from nucleotide position 3210 through position 3107 can be viewed a polymer or oligomer that contains eight XGNZG pentapeptides repeated. Each of above polymers or oligomers contains a plurality of the pentapeptide repeating units bonded together by peptide bonds.

Solid phase peptide synthesis techniques, as are described in the before-discussed U.S. Patents whose disclosures are incorporated herein by reference, are typically the most useful means of preparation for oligomers and pollFmers containing up to a total of about forty total residues (eight repeating pentapeptide units).

Genetic engineering techniques as are described herein are particularly useful for preparing larger polymers that contain more than about eight pentapeptide repeating units. For example, a double stranded DNA molecule having the sequence shown in FIG. 2 from nucleotide position 2959 through nucleotide position 3303, and in phase with the illustrated amino acid residue sequence of protein 517 can be excised from the larger molecule shown in FIG. 2 or synthesized from appropriate deoxyribonucleic acid derivatives using known techniques, and thereafter ligated into an appropriate plasmid vector for expressing a peptide polymer that corresponds substantially in sequence to the polymer containing the pentapeptide repeating units shown beneath the sequence at those positions in FIG. 2.

Higher molecular weight polymers; i.e., with average molecular weights of about 10,000 to 1,000,000, or more, containing one or more of the above 540 protein or 517 protein pentapeptide repeating units can also be prepared by oxidatively polymerizing a peptide that is terminated with cysteine (Cys; C) residues, or a "diCys-terminated" peptide. The resulting polymer thereby contains its repeating units bonded together by oxidized cysteine (cystine) disulfide bonds.

For example, each of the before-discussed 40 protein peptides or 517 protein pentapeptides can be synthesized to contain an additional Cys residue at each of the amino- and carboxy-termini to provide diCys-terminated peptides in their reduced forms. After synthesis, in a typical laboratory preparation, 10 milligrams of the diCys peptide (containing cysteine residues in un-oxidized form) are dissolved in 250 milliliters (ml) of 0.1 molar (M) ammonium bicarbonate buffer. The dissolved diCys-terminated peptide is then air oxidized by stirring the resulting solution gently for period of about 18 hours in the air, or until there is no detectable free mercaptan by the Ellman test. [See Ellman, *Arch. Biochem. Biophys.*, 82:70–77 (1959).]

The polymer so prepared contains a plurality of the synthetic, peptide repeating units that are bonded together by oxidized cysteine (cystine) residues. Such polymers typically contain their peptide repeating units bonded together in a head-to-tail manner as well as in head-to-head and tail-to-tail manners; i.e., the amino-termini of two peptide repeating units can be bonded together through a single cystine residue as can two carboxyl-termini since the linking groups at both peptide termini are identical.

A 517 protein pentapeptide repeating unit can itself be contained in the form of an oligomer containing up to about eight pentapeptide repeating units, or in a shorter peptide such as the 14-residue Peptide 57. Still further, a genetically engineered polypeptide such as that prepared from the DNA sequence of nucleotides at positions 2959 through 303 that has been further engineered to include codons for Cys (TGT or TGC ) at the 5'- and 3'-ends can also be polymerized.

The molecular weight of such a polymer can be controlled through the addition of chain-terminating reagents. Exemplary chain terminating reagents are cysteine itself and a peptide such as a before-described pentapeptide that further includes a single Cys residue, preferably at a terminus.

The full names for individual amino acid residues are sometimes used herein as are the well-known three letter abbreviations. One letter abbreviations (code) is also utilized. The Table of Correspondence, below, provides the full name as well as the three letter and one letter abbreviations for each amino acid residue named herein (See, for example, L. Stryer, *Biochemistry*, 2nd ed., W. H. Freeman and Company, San Francisco, (1981), page 16). The amino acid residues utilized herein are in the-natural, L, form unless otherwise stated.

Table of Correspondence

| Amino acid | Three letter abbreviation | One letter symbol |
| --- | --- | --- |
| Alanine | Ala | A |
| Arginine | Arg | R |
| Asparagine | Asn | N |
| Aspartic acid | Asp | D |
| Asparagine or aspartic acid | Asx | B |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

III. MATERIALS AND METHODS

A. Recombinant studies

1. Bacteria, Phage and Plasmids

The *E. coli* strains used in this work were BNN97 [Young et al., (1983) *Science*, 222:778–782; ATCC 37194]; JM83 [Yanisch-Perron et al., (1985), *Gene*, 33:103–119; also ATCC 35607]; JM101 [Yani sch-Per ton et al., (1985), *Gene*, 33:103–119; also ATCC 33876]; Y1089 [Young et al., (1983), *Science*, 222:778–782; also ATCC 37196]; and Y1090 [Young et al., (1983), *Science*, 222:778–782; also ATCC 37197]. Plasmids pUC19 [Yanisch-Perron et al., (1985), *Gene*, 33:103–119] and pMC1871 [Shapira et al., (1983), *Gene*, 25:71–82] were purchased from Pharmacia Fine Chemicals, Piscataway, N.J. The recombinant DNA library of *M. tuberculosis* genomic DNA fragments in the λgt11 vector was constructed by R. Young et al. (1985), *Proc. Natl. Acad. Sci. USA*, 82:258 3–2587, and made available through the World Health Organization's Program for Research in the Immuno logy of Tuberculosis. Recombinant phage λRY3143 and λRY3146 were generously provided R. A. Young [Whitehead Institute, M.I.T.; Young et al., ( 1985), *Proc. Natl. Acad. Sci. USA*, 82:2583–2587]. Subclones of the mycobacterial DNA inserts in these recombinant phage were constructed in pUC19 or M13mp9 [Messing et al., (1982), *Gene*, 9:269–276; M13mp9 is listed for sale in the August, 983 catalog of Bethesda Research Laboratories, Inc.] vectors using standard recombinant DNA techniques [Maniatis et al., (1982), *Molecular Cloning—a laboratory manual*, Cold Spring Harbor Laboratory, Cold Spring Harbor, N.Y.].

2. Antisera

Monoclonal antibodies specific for the 65KD antigen were obtained from the Immunology of Tuberculosis Scientific Working Group under a grant from the WHO/World Bank/UNDP Special Program for Vaccine Development. These antibodies included IT-13 [WTB-78; Coates et al., (1981), *Lancet*, 2:167–169]; IT-31 [SA2D5H4; T. Buchanon, unpublished] and IT-33 [MLIIH9; Gillis et al., (1982), *Infect. Immun.*, 37:172–178]. Anti-beta-galactosidase antibodies were purchased from Cooperbiomedical, Malvern, PA. Polyclonal rabbit antisera directed against a sonicate of

*M. tuberculosis* strain H37Rv were elicited as previously described [Minden et al., (1984), *Infect. Immun.*, 46:519–525].

3. Immunoscreening of λgt11-M. Tuberculosis Library

Clones reactive with the monoclonal antibodies specific for the 65KD antigen were isolated essentially as described by Young et al. [Young et al., *Proc. Natl. Acad. Sci. USA*, 82:2583–2587]. Briefly, for each 150 mm LB plate, 0.6 ml of a fresh overnight culture of Y1090 cells were infected with 1–2×10$^5$ plaque-forming units (pfu) of the library. After 3.5–4 hours of growth at 42° C. the plaques were overlaid with a dry nitrocellulose filter that had been saturated with 10 millimolar (mM) isopropyl-beta-D-thiogalactopyranoside (IPTG; available from Sigma Chemical Co.). The plates were incubated an additional 3.5–4 hours at 37° C. and then removed to room temperature and the position of the filters marked.

The filters were washed briefly in TBST [50 mM Tris-HCl, pH 8,150 mM NaCl, 0.05% Tween 20 [polyoxyethylene (20) sorbitan monolaurate]] and then incubated in TBST plus 20% fetal calf serum. After 30 minutes at room temperature, the filters were transferred to TBST plus antibody.

For the initial screen, the antibody mix contained a 1:1000 dilution of admixed IT-13, IT-31, and IT-33. The filters were incubated with the antibody solution overnight at 4° C. with gentle agitation, washed in TBST and reacted with biotinylated goat anti-mouse immunoglobulin, the Vectastain ABC reagent, and developer as described by the manufacturer (Vector Laboratories, Burlingame, Calif.). After the color had developed, the filters were washed with several changes of water and air dried.

Phage corresponding to positive signals were twice plaque-purified. To determine which monoclonal antibodies reacted with which of the recombinant phage, about 100 pfu of a purified phage stock were inoculated in a small spot on a lawn of Y1090 *E. coli* on an LB (Luria-Bertani broth) plate. The phage were allowed to grow and induced to synthesize the foreign proteins as described above. The filters were then reacted with a 1:1000 dilution of one of the monoclonal antibodies. The subsequent steps were the same as for the initial screen.

4. Western Blot Assays

Cells containing phage or plasmids in which the expression of the foreign sequences was under the control of the *E. coli* lac gene regulatory sequences were induced to synthesize the foreign proteins by incubating the cells in the presence of 2.5 mM IPTG for 2 hours. Crude lysates of cells expressing λgt11 recombinants were made as described in Huynh et al; (1985), *DNA Cloning Techniques: A Practical*; Gover, ed., IRL Press, Oxford, Vol. I, pp. 49–78. Briefly, those lysates were made by harvesting cells from overnight cultures and resuspending the cells in 10 mM Tris pH 7.5, 10 mM EDTA containing 100 ug lysozyme/ml. After 10 minutes at room temperature, sodium dodecyl sulfate (SDS) was added to a final concentration of 0.5%. A protease inhibitor (Trasylol, Boehringer Mannheim, Indianapolis, Ind.) was added to all crude lysates at a final concentration of 0.03%–0.3%.

The crude protein preparations were electrophoresed on 10% polyacrylamide-SDS Laemmli gels [Laemmli, (1970) *Nature*, 227:680–685], and the separated proteins electrophoretically transferred to nitrocellulose [Towbin et al., (1979), *Proc. Natl. Acad. Sci . USA*, 76:4350–4354]. The immobilized proteins were reacted with a 1:1000 dilution of monoclonal antibody IT-13 in TBST overnight at 4° C. The nitrocellulose filters were then washed, reacted with peroxidase-conjugated goat anti-mouse immunoglobulin, and developed as previously described [Niman et al., (1983), *Proc. Natl. Acad. Sci. USA*, 80:4949–4953].

5. Nucleic Acid Sequencing

The sequences of 5'-end-labeled restriction fragments of the mycobacterial DNA were determined by a modification of the partial chemical degradation technique of Maxam and Gilbert [Brow et al., (1985), *Mol. Biol. Evol.*, 2:1–12; and Maxam et al., (1976), *Proc. Natl. Acad. Sci. USA*, 74:560–564]. For the M13/dideoxy sequencing studies, Sau3AI fragments from the mycobacterial DNA inserts were subcloned into the BamHI site of M13mp9. Phage DNA was isolated from the M13 recombinants and subjected to the dideoxy chain termination sequencing reactions [Biggin et al., (1983), *Proc. Natl. Acad. Sci. USA*, 80:3963–3965; and Sanger et al., (1980), *J. Mol. Biol.*, 143:161–178]. The products of the sequencing reactions were electrophoresed on 6% acrylamide/7M urea/0.5–2.5xTBE gradient sequencing gels, [Biggin, (1983), *Proc. Natl. Acad. Sci. USA*, 80:3963–3965]. The gels were dried under vacuum and exposed to Kodak XRP-1 film. The nucleotide sequences were determined independantly for both strands of the mycobacterial DNA.

Computer-aided analyses of the nucleic acid sequences and deduced protein sequences were performed using the databases and programs provided by the Nucleic Acid and Protein Identification Resources of the National Institutes of Health as well as the programs of Chow et al., (1978) *Adv. Enzym.*, 47:45–148 and Hopp and Woods [Hopp et al., (1981), *Proc. Natl..Acad. Sci. USA*, 78:3824–3828].

6. Beta-galactosidase assays

Cells were grown in B broth or B broth plus 2.5 mM IPTG to an optical density at 600 nanometers ($OD_{600}$) of about 0.3. Crude lysates were made, and beta-galactosidase was activity assayed as described by Miller (1972), *Experiments in Molecular Genetics*, Cold Spring Harbor Laboratory, Cold Spring Harbor, N.Y.

7. Capacity of Recombinants to Elicit DCH a. DCH Assays

Studies were carried out to determine whether the recombinant proteins or purified protein derivative (PPd) (Connaught Laboratories, Ltd., Willowdale, Canada) would elicit DCH reactions in Hartley guinea pigs that had been immunized with sonicates of *M. tuberculosis, M. bovis* or saline. Groups of guinea pigs were given three weekly intramuscular (i.m.) injections of sonicates suspended in incomplete Freund's adjuvant (IFA) as the physiologically tolerable diluent. Each injection contained 1.0 milligram (rag) of protein. Some animals received a fourth injection so that one week after the final injection, all animals were tested intradermally (i.d). Test antigens included the crude and partially purified recombinant extracts as well as saline and PPd as controls. Test antigens were used at 1–10 ug diluted in 100 ul of phosphate-buffered saline at a pH value of pH 7.0 (PBS), containing 0.0005% Tween 20 as the physiologically tolerable diluent. Groups of unimmunized guinea pigs were similarly tested. All i.d. injections were administered into shaved areas on guinea pig flanks. Reactions were read at 24, 48 and 72 hours, and were considered positive when the diameters of erythema and indurated areas exceeded 10 mm.

b. Preparation of Crude Lysates

E. coli containing a plasmid or lambda phage of interest were grown by incubation at 37 degrees C with aeration in B-broth to late phase in which absorbance at 600 nanometers ($A_{600}$) was between approximately 0.4 and 0.6. IPTG was then added to a final concentration of 10 mM and the bacteria were further incubated for two hours.

The bacterial culture was then chilled on ice for 10 minutes and the cells were harvested by centrifugation at 6000 rpm for 10 minutes. The resulting cell pellet was washed once in TBS (50 mM Tris, pH 8,150 mM NaCl) by resuspension and recentrifugation, and was thereafter resuspended (Sigma Chemical Co., St. Louis, Mo.) in a volume of TBS with 0.5 molar sucrose equivalent to 1/10 the original culture volume. Lysozyme was added to the resulting resuspended solution to a final concentration of 50 ug/ml, and that admixture was incubated for 10 minutes at 37 degrees C. Cells were harvested by centrifugation and were resuspended in an equal volume of TBS. Thereafter, DNAse, Trasylol and SDS (Sigma) were added to the resulting admixture such that the final concentrations were 1 ug/ml, 0.1% and 1%, respectively. That admixture was further incubated at room temperature for a time period of 10 minutes with periodic mixing to effect completion of cell lysis. The resulting crude lysate was stored at –20 degrees C until use.

c. Partial Purification of
Expressed 65KD Protein

Proteins containing the 65KD antigens were partially purified from crude lysates of E. coli expressing that protein by differential ammonium sulfate precipitation. To that end, a crude lysate was first combined with a solution of saturated ammonium sulfate (SAS) to give a final concentration of 30% of the original lysate concentration. Precipitation was effected as is well known in the art, and the resulting supernate was retained. The supernate was then combined with SAS to give a concentration of 50% of that of the original lysate, and precipitation effected again. The resulting pellet was retained, resuspended in PBS and dialysed against PBS. This resulting dialysed material is referred to as partially purified.

d. Preparation of Extracts of M. tuberculosis

M. tuberculosis strain H37Rv and M. bovis strain BCG were obtained from the culture collection Of the National Jewish Hospital and Research Center, Denver, Co., and grown as previously described [Minden et al., (1977) Science, 176:57–58 and Minden et al., (1972) Infect. Immun., 6:574–582].

Bacteria were then heat-killed and broken by sonication with ultrasonic treatment until, by microscopic examination, greater than 95% of the cells were disrupted. These disrupted bacteria were then subjected to ultracentrifugation at 200,000xg for a time period of 2 hours, and the supernate was retained. The supernates so obtained are referred to as H37Rv-S and BCG-S, repectively, and their antigenic and biological characteristics have been described.

B. Peptide Studies
1. Mycobacterial antiqens

Armadillo derived killed M. leprae was supplied by Dr. R. J. W. Rees, Mill Hill in London, from the IMMLEP (WHO) bank. M. tuberculosis and M. bovis BCG were kindly donated by Dr. Eng, National Institute of Public Health, Oslo, Norway. Bacilli were killed by irradiation (2.5 m rad). Recombinant M. tuberculosis 65 KD antigen, expressed from λgt11 as a beta-galactosidase fusion protein, were purified from E. coli lysates prepared as described in Oftung et al., (1987) J. Immunol., 138:927–931 on a high affinity anti-beta-galactosidase column (Promega Biotech, Madison, USA).

2. Synthetic peptides

The protected peptide resins were prepared by usual Merrifield solid phase techniques in groups of 100 by the method of Simultaneous Multiple Peptide Synthesis [Houghten, (1985) Proc. Natl. Acad. Sci. USA, 82:5131–5135; and Houghten et al., (1985) Inter. J. Pept. Prot. Res., 27:673–678], and were cleaved twenty-four at a time in a new multi-vessel apparatus [Houghten et al., (1986) Biotechniques, 4:522–529]. Each synthesis resulted in the generation of 50–75 mg of peptide. Typical purities of the crude peptides ranged from 65–95%.

3. T-cell clones and lines

The T-cell clone K8AH from a tuberculosis patient (AH) and the T-cell clone A7JM from a killed M. leprae-vaccinated person (JM) were established by the limiting dilution technique as described [Oftung et al., (1987) J. Immunol., 138:927–931]. The T-cell line was raised from peripheral blood mononuclear cells (PBMC) of the donor JM by stimulation of $2\times10^6$ PBMC/ml in complete medium (RPMI 1640+15% AB serum +1% penicillin and streptomycin) with M. bovis BCG (20 ug/ml) in 24-well Costar plates. After 6 days of incubation at 37° C. in an atomsphere of 5% $CO_2$ and 95% air, antigen-reactive cells were expanded by adding 100 U/ml recombinant IL-2 two times per week. After long term storage in liquid nitrogen, T cells were propagated in vitro by stimulation of $2\times10^5$ cells/ml in 24 well Costar plates with whole bacilli as antigen (20 ug/ml) in the presence of $10^6$ irradiated autologous PMBC as feeder (antigen-presenting) cells and recombinant IL-2 (100 U/ml). Efficient expansion of clones and lines was achieved by stimulation with antigen and feeder cells once and IL-2 twice per week. Determination of T cell subsets was performed as previously described [Oftung et al., (1987) J. Immunol., 138:927–931].

4. Peptide-Induced T Cell Clone Stimulation Assays

The following assays were carried out for the inventors by Dr. Frederik Of tung, at the Laboratory for Immunology, Norwegian Radium Hospital, Oslo, Norway. Initial assays for T cell stimulation were carried out using coded samples.

a. Antigen-Induced Proliferation of T-cell Clones and Lines

Clonal ($1\times10^4$) or polyclonal ($2\times10^4$) T cells and irradiated autologous PBMC ($1\times10^5$) were distributed to each well of 96-well flat bottom Costar plates. Mycobacterial antigens as whole bacilli, recombinant antigens as affinity-purified material or synthetic peptides were then added in triplicates or duplicates. The total culture volume was kept at 200 microliters (ul).

After 72 hours of incubation, the cultures were given a 4 hour pulse of 0.045 mBq [$^3$H]-thymidine (specific activity= $185\times10^3$ mBq/mM). Cells were then harvested and radioactivity incorporated was determined by liquid scintillation counting [Mustafa et al., (1983) Clin. Exp. Immunol., 52:29–37].

The results are expressed as mean (triplicates or duplicates) values of counts per minute (cpm). Cells were considered to be proliferating in response to a given antigen where cpm in cultures with antigen minus cpm in cultures without antigen was more than 1000 and cpm in cultures with antigen divided by cpm in cultures without antigen was more than 2.

b. Lymphokine Production and Assay

T-cell clones ($2\times10^5$ cells/ml) were distributed to wells of 24-well Costar plates with adherent cells from $1\times10^6$ irradiated autologous PBMC plus antigen at optimal concentrations. Cell free supernatants were collected after 16 or 48 hours of incubation and stored at minus 20° C. until assayed for lymphokine activities. IL-2 activity in supernatants harvested after 16 hours of incubation was determined by their ability to stimulate an IL-2-dependent mouse T-cell clone (CTLL 2) to proliferate [Mustafa et al., (1985) *Clin. Exp. Immunol.*, 62:474–481]. Granulocyte macrophage-CSF (GM-CSF) activity in the same supernatants was assayed by the capacity of the supernatants to induce colony formation in mononuclear bone marrow cells [Dahl et al., (1972) *Acta Pathol. Microbiol. Scand. Sect. B*, 80:863–870]. Supernatants harvested after 8 hours were used to determine interferon-gamma activity by the method of Dahl and Degree [Acta *Pathol. Microbiol. Scand. Sect. B*, 80:863–870], using human embryonic lung fibroblasts and vesicular stomatitis virus as the challenge virus.

c. Cytotoxicity assay

Adherent cells from 1×10⁶ autologous irradiated PBMC in 24-well Costar plates were pulsed with antigens at optimal concentrations and the density of T cell clones was adjusted to 1×10⁵ cells/well. After 7 days of incubation, T cells were washed off, and 0.5 ml of 0.03% neutral red (in saline +10% FBS) were added to each well and the plates incubated for 30 minutes. Neutral red was then removed from the wells by washing, and the dye taken up by macrophages was released by adding 0.5 ml of 0.05M acetic acid in 50% ethanol [Parish et al., (1983) J. Immunol. Methods, 58:225]. Percentage cytotoxicity was calculated from spectrophotometric absorbance measurement at 540 nanometers [$OD_{540}$] according to the formula:

$$\text{Cytotoxicity (\%)} = \frac{OD_{540} \text{ con.} - OD_{540} \text{ study}}{OD_{540} \text{ con.}}$$

where $OD_{540}$ con.=$OD_{540}$ of control cultures with adherent cells + T-cell clones; and $OD_{540}$ study=$OD_{540}$ of study cultures with adherent cells+T-cell clones+antigen.

5. Peptide-Induced Pooled T Cell Stimulation

Stimulation assays of pooled human T cells were carried out for the inventors by Dr. Stefan Kaufman of the Max Plank Institute for Immunology, Freiberg, West Germany. Again, coded samples were supplied for the assays.

The assay procedure was as follows. Mononuclear cells were isolated from peripheral blood of *M. bovis* BCG-vaccinated persons on Ficoll-Hypaque gradients [Emmerich et al., (1986) *J. Exp. Med.*, 163:1024–1029; and Boyum, (1968) *Scand. J. Clin. Lab. Invest.,* 21 (Suppl. 97) :31], and were used to seed wells of a 96-well microtiter plate at about $2\times10^5$ cells/well. Antigen was then added at 0.1 ug/ml, 1 ug/ml and 10 ug/ml.

After six days of culture, 1 microCurie (uCi) of [$^3$H]-thymidine was added to each well. Eighteen hours later, cultures were harvested on glass fiber filters. Thymidine incorporation was measured in a liquid scintillation counter.

For the assays of Table 5, the PBMC were pooled. For the studies conducted related to HLA restrictions, the PBMC were kept separate and the HLA alleles ascertained by standard techniques.

The present invention has been described with respect to preferred embodiments. It will be clear to those skilled in the art that modifications and/or variations of the disclosed subject matter can be made without departing from the scope of the invention set forth herein.

What is claimed is:

1. A method for ascertaining the presence of human T cells in a body sample that are immune to *M. tuberculosis* or *M. bovis* comprising the steps of:

(a) admixing and contacting human T cells to be assayed in an aqueous culture medium with a stimulatory amount of both antigen-presenting cells and a mycobacterial peptide antigen to form a stimulatory cell culture, said mycobacterial peptide antigen consisting essentially of (i) a peptide whose amino acid residue sequence is selected from the group consisting of A V L E D P Y I L L V S S K V;
L L V S S K V S T V K D L L P;
L L P L L E K V I G A G K P L;
A I L T G G Q V I S E E V G L;
I A F N S G L E P G V V A E K;
A R R G L E R G L N A L A D A V K V;
E K I G A E L V K E V A K K;
G L K R G I E K A V E K V T E T L; and
I E D A V R N A K A A V E E G; or (ii) a polymer comprising a plurality of peptide units whose sequences are listed in (i), and which units are bonded together by oxidized cysteine residues present at the termini of said units;

(b) maintaining said stimulatory cell culture for a time period sufficient for mycobacterially-immune T cells present to be stimulated and to evidence stimulation; and (c) determining the presence of T cell stimulation.

2. The method of claim 1 wherein said method is carried out in vivo, said antigent-presenting cells are provided endogenously and said aqueous culture medium is endogenous blood or lymph.

3. The method of claim 1 wherein said method is carried out in vitro, and said stimulation is determined by an assay selected from the group consisting of (i) T cell proliferation, (ii) interleukin-2 secretion, (iii) interferon-gamma secretion, (iv) granulocyte macrophage-colony stimulating factor secretion and (v) cytotoxicity.

4. The method of claim 1 wherein said peptide antigen is present as a polymer having units comprised of said mycobacterial peptide antigen, and said peptide antigen units are bonded together by oxidized cysteine residues at the termini thereof.

5. A assay kit comprising a container that

I, includes a mycobacterial antigen present in an amount to carry out at least one assay for the presence of human T cells that are immune to *M. tuberculosis* or *M. bovis*, said mycobacterial antigen consisting essentially of (i) a peptide whose amino acid residue sequence is selected from the group consisting of A V L E D P Y I L L V S S K V;
L L V S S K V S T V K D L L P;
L L P L L E K V I G A G K P L;
A I L T G G Q V I S E E V G L;
I A F N S G L E P G V V A E K;
A R R G L E R G L N A L A D A V K V;
E K I G A E L V K E V A K K;
G L K R G I E K A V E K V T E T L; and
I E D A V R N A K A A V E E G; or (ii) a polymer comprising a plurality of peptide units whose sequences are listed in (i), and which units are bonded together by oxidized cysteine residues present at the termini of said repeating units.

* * * * *

UNITED STATES PATENT AND TRADEMARK OFFICE
CERTIFICATE OF CORRECTION

PATENT NO. : 5,478,726
DATED : December 26, 1995
INVENTOR(S) : Shinnick et al.

It is certified that error appears in the above-indentified patent and that said Letters Patent is hereby corrected as shown below:

Column 1, lines 4-6, delete the first paragraph and insert the following heading and paragraph in its place:

--Governmental Support and Rights

This invention was made with government support under Contract No. AI22217 by the National Institutes of Health. The government has certain rights in the invention.--

Signed and Sealed this

Twenty-first Day of May, 1996

*Attest:*

BRUCE LEHMAN

*Attesting Officer*   *Commissioner of Patents and Trademarks*